United States Patent
Apelqvist et al.

(10) Patent No.: US 6,492,424 B1
(45) Date of Patent: Dec. 10, 2002

(54) GLUCOCORTICOID AND THYROID HORMONE RECEPTOR LIGANDS FOR THE TREATMENT OF METABOLIC DISORDERS

(75) Inventors: Theresa Apelqvist, Huddinge (SE); Patrick Goede, Tumba (SE); Erik Holmgren, Gustavsberg (SE)

(73) Assignee: Karo Bio AB, Huddinge (SE)

( * ) Notice: Subject to any disclaimer, the term of this patent is extended or adjusted under 35 U.S.C. 154(b) by 0 days.

(21) Appl. No.: 09/744,865

(22) PCT Filed: Aug. 4, 1999

(86) PCT No.: PCT/IB99/01447

§ 371 (c)(1),
(2), (4) Date: Apr. 9, 2001

(87) PCT Pub. No.: WO00/07972

PCT Pub. Date: Feb. 17, 2000

(30) Foreign Application Priority Data

Aug. 5, 1998 (GB) .............................. 9816935

(51) Int. Cl.[7] ...................... A61K 31/19; A61K 31/185; C07C 62/32; C07C 65/40; C07C 65/00

(52) U.S. Cl. ...................... 514/570; 514/563; 514/569; 514/576; 514/577; 562/460; 562/462; 562/463; 562/465; 562/472; 562/474; 562/475; 560/170; 560/171

(58) Field of Search .................. 562/472, 460, 562/462, 463, 465, 474, 475; 560/170, 171; 514/563, 569, 570, 576, 577

(56) References Cited

U.S. PATENT DOCUMENTS 5,569,674 A * 10/1996 Yokoyama et al.

OTHER PUBLICATIONS

Yokoyama et al, Synthesis and Structure–Activity Relationships of Oxamic Acid and Acetic Acid Derivatives Related to L–Thyronine, 1995, Journal of Medicinal Chemistry, 38, pp. 695–707.*

* cited by examiner

Primary Examiner—Johann Richter
Assistant Examiner—Paul A. Zucker
(74) Attorney, Agent, or Firm—Todd E. Garabedian; Wiggin & Dana LLP

(57) ABSTRACT

Novel glucocorticoid and thyroid receptor ligands as provided which have the general formula (I):

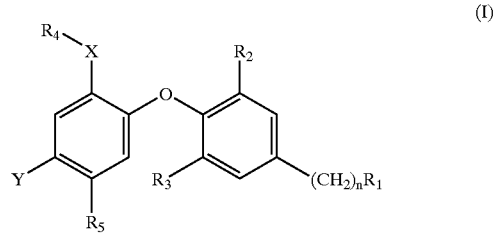

in which $R_1$ is an aliphatic hydrocarbon, an aromatic hydrocarbon, carboxylic acid or ester thereof, alkenyl carboxylic acid or ester thereof, hydroxy, halogen, or cyano, or a pharmaceutically acceptable salt thereof. $R_2$ and $R_3$ are the same or different, and are hydrogen, halogen, alkyl of 1 to 4 carbons, or cycloalkyl of 3 to 5 carbons, at least one of $R_2$ and $R_3$ being other than hydrogen. X is carbonyl or methylene. $R_4$ is an aliphatic, aromatic or heteroaromatic. Y is hydroxyl, methoxy, amino, or alkyl amino. n is an integer from 0 to 4. A method for treating diseases associated with metabolism dysfunction or which are dependent on the expression of a glucocorticoid or thyroid receptor gene such as diabetes, hypercholesterolemia, or obesity using these compounds is also disclosed.

18 Claims, No Drawings

GLUCOCORTICOID AND THYROID HORMONE RECEPTOR LIGANDS FOR THE TREATMENT OF METABOLIC DISORDERS

This is a §371 application of PCT/IB99/01447 filed Aug. 4, 1999.

FIELD OF THE INVENTION

This invention relates to novel compounds that are liver-selective glucocorticoid receptor antagonists and liver-selective thyroid receptor agonists, to methods of preparing such compounds, and to methods for using such compounds in the regulation of metabolism, especially lowering serum glucose and low density lipoprotein levels.

BACKGROUND OF THE INVENTION

Glucocorticoid Receptor Antagonists

A major problem with both Type 2 and Type 1 diabetes is that there is excessive and inappropriate production of glucose by the liver. This abnormality is the primary cause of fasting hyperglycemia and occurs in addition to defects in regulation of insulin release and in peripheral sensitivity to insulin. Thus, agents that decrease liver glucose production would be beneficial for treating both Type 2 and also Type 1 diabetes.

Intensive treatment of the hyperglycemia of Type 1 diabetes mellitus has been shown markedly to decrease the development of ocular renal and neuropathic complications, and there is evidence that intensive treatment is also beneficial for Type 2 diabetes. The available data also indicate that most patients are currently not receiving ideal and state-of-the-art treatment for either Type 2 or Type 1 diabetes. This inadequacy exists in spite of the availability of several different types of preparations of insulin for treatment of both Type 2 and Type 1 diabetes, and of a number of additional modalities, including agents that stimulate insulin release (e.g., sulfonylureas), influence liver glucose production (e.g., metformin), affect the sensitivity to insulin (e.g., troglitazone) and glucose absorption (e.g., α-glucosidase inhibitors). In spite of the availability of several different orally-active agents that lower blood glucose levels. many patients with Type 2 diabetes also require insulin for control of their blood sugar levels. Overall, insulin usage in Type 2 diabetes exceeds that for Type 1 diabetes, and there is general agreement that there is a need for additional orally-active agents to treat Type 2 diabetes.

The glucocorticoid secretions of the adrenal gland (dominantly cortisol in humans) were so named because of their ability to regulate glucose metabolism. These steroids stimulate the production of glucose in the liver by promoting gluconeogenesis, which is the biosynthesis of new glucose (i.e. not glucose from glycogen). Thus, in glucocorticoid insufficiency there is a tendency to hypoglycemia, with decreased liver glucose production. Further development of Addison's disease in the diabetic patient generally leads to lowered glucose levels. Conversely, glucocorticoid excess can provoke frank diabetes in individuals with latent diabetes mellitus, and generally aggravates glycemic control in established diabetic patients. Similar influences have been observed in various animal models.

The increased glucose production in response to glucocorticoids is due to effects on a number of proteins. Important among these are effects on various transaminases that convert amino acids to glucose precursors, and induction of glucose-6 phosphatase and phosphoenolpyruvate carboxykinase (PEPCK). Even a modest increase of PEPCK, as obtained in transgenic mice, gives rise to hyperglycemia. In mice with Type 2 diabetes and increased levels of corticosterone (the endogenous glucocorticoid of that species) there is increased expression of PEPCK. This over expression of PEPCK can be repressed by treatment with the known GR antagonist RU486 with a concomitant decrease in the hyperglycemia.

The considerations outlined above indicate that if the action of endogenous glucocorticoids on liver glucose production could be blocked in a specific manner, glycemic control could be improved for the benefit of the diabetic patients. However, to date, all means to block glucocorticoid action have been general. Thus, adrenalectomy leaves the patient with frank adrenal insufficiency and the problems of Addison's disease. Blockade of adrenal steroid production, for example by metyrapone, or of glucocorticoid action, for example with RU486, is ordinarily of limited duration of effectiveness and when it is effective also results in generalized adrenal insufficiency. Long term compensatory ACTH hypersecretion and increased cortisol release that override the block generally overcome these treatments. By contrast, a liver-specific GR antagonist would not have these problems, should counteract the increased liver glucose production in diabetes mellitus, and should be useful for treatment of Type 2 diabetes.

A liver selective GR antagonist offers a number of advantages. First, it should decrease liver glucose production. This action will have a significant effect on glycemic control. In fact, excessive liver glucose production can be the major defect in Type 2 diabetes. Secondly, such a drug should enhance insulin sensitivity because of the overall improvement in the metabolic milieu and the amelioration of the hyperglycemia-induced defects in insulin action and secretion. The decreased demand on β-cell secretion, as a result of a reduction in glycemia, would retard the progressive β-cell dysfunction characteristic of Type 2 diabetes. Another advantage of GR antagonist treatment compared with sulfonylurea or insulin treatment is that the patient would run a lower risk of hypoglycemia.

Previous efforts to block glucocorticoid action in diabetes have been hampered by the fact that any compounds used would generally block glucocorticoid action in all tissues and would lead to the potential problems of glucocorticoid insufficiency, such as hypotension, shock, and ultimately death if the organism were exposed to sufficiently-strong stress conditions. In contrast, a liver-selective GR-antagonist with minimal effects outside the liver could be used as a front-line therapy for Type 2 diabetes, or could be used in conjunction with other existing therapies.

Thyroid Hormone Receptor Antagonists

Thyroid hormones affect the metabolism of virtually every cell of the body. At normal levels. these hormones maintain body weight, the metabolic rate, body temperature, and mood, and influence serum low density lipoprotein (LDL) levels. Thus, in hypothyroidism there is weight gain, high levels of LDL cholesterol, and depression. In excess with hyperthyroidism, these hormones lead to weight loss, hypermetabolism, lowering of serum LDL levels, cardiac arrhythmias, heart failure, muscle weakness, bone loss in postmenopausal women, and anxiety.

Thyroid hormones are currently used primarily as replacement therapy for patients with hypothyroidism. Therapy with L-thyroxine returns metabolic functions to normal and can easily be monitored with routine serum measurements of levels of thyroid-stimulating hormone (TSH), thyroxine (3,5,3', 5'-tetraiodo-L-thyronine, or $T_4$) and triiodothyronine (3,5,3'-triiodo-L-thyronine, or $T_3$). However, certain of the deleterious effects of thyroid hormones limit the rapidity with which replacement therapy can be given and in some circumstances, particularly in older individuals, even completely exclude replacement therapy.

In addition, some effects of thyroid hormones may be therapeutically useful in non-thyroid disorders if adverse effects can be minimized or eliminated. These potentially-useful influences include weight reduction, lowering of serum LDL levels, amelioration of depression and stimulation of bone formation. Prior attempts to utilize thyroid hormones pharmacologically to treat these disorders have been limited by manifestations of hyperthyroidism, and in particular by cardiovascular toxicity.

Development of liver specific and selective thyroid hormone receptor agonists could lead to specific therapies for lowering of serum LDL levels while avoiding the cardiovascular and other toxicities of native thyroid hormones. Tissue-selective thyroid hormone agonist may be obtained by selective tissue uptake or extrusion, topical or local delivery, targeting to cells through other ligands attached to the agonist.

DESCRIPTION OF THE INVENTION

In accordance with the present invention, compounds are provided which are glucocorticoid and thyroid hormone receptor ligands, and have the general formula I:

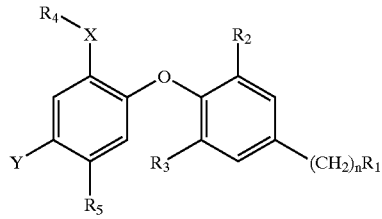

in which:
  $R_1$ is an aliphatic hydrocarbon, an aromatic hydrocarbon, a carboxylic acid or ester thereof, alkenyl carboxylic acid or ester thereof, hydroxy, halogen, or cyano, or a pharmaceutically salt thereof, and all stereoisomers thereof;
  $R_2$ and $R_3$ are the same or different and are hydrogen, halogen, alkyl of 1 to 4 carbons or cycloalkyl of 3 to 6 carbons, at and least one of $R_2$ and $R_3$ being other than hydrogen.
  X is carbonyl (C=O) or methylene ($CH_2$).
  $R_4$ is an aliphatic, other than $C_1$ aromatic, heteroaromatic or cycloaliphatic group
  $R_5$ is hydrogen, halogen, alkyl of 1 to 4 carbons, cycloalkyl of 3 to 6 carbons or cycloalkyl alkyl of 5 to 8 carbons.
  Y is hydroxyl, methoxy, amino, alkyl amino or amide.
  Preferably, L is a linear or branched $C_2$ to $C_6$ alkyl more preferably t-butyl.
  $R_2$ and $R_3$ are preferably halogen or a halogenated alkyl, more preferably bromine or another hydrophobic group of similar size to bromine. A possible halogenated alkyl is —$CF_3$.
  In the $(CH_2)_n$ $R_1$ side chain n is preferably 1.
  $R_1$ is an acidic or negatively-charged group, and carboxylic acid or a bioisoster of carboxylic acid is preferred. Bioisosters of carboxylic acids are groups that display the same receptor-binding activity and thus, in general. the same in vivo activity. Examples are tetrazole, acylsulphonamides, phosphonates, and sulphonates.

In addition, in accordance with the present invention, a method for preventing, inhibiting, or treating a disease associated with a metabolic dysfunction or which is dependent upon the expression of a glucocorticoid or thyroid hormone receptor regulated gene is provided, wherein a compound of formula I is administered in a therapeutically effective amount. The compound of formula I is preferably also liver selective. Examples of such diseases associated with metabolic dysfunctions or are dependent upon the expression of a glucocorticoid receptor regulated gene are set out hereinafter and include diabetes and inflammation. Examples of such diseases that are dependent upon expression of thyroid hormone receptor regulated gene include obesity, hypercholoesterolemia, atherosclerosis, cardiac arrhythmias, depression, osteoporosis, hypothyroidism, goitre, thyroid cancer as well as glaucoma and congestive heart failure.

DETAILED DESCRIPTION OF THE INVENTION

The following definitions apply to the terms as used throughout this specifications. unless otherwise limited in specific instances.

The term "glucocorticoid receptor ligand" as used herein is intended to cover any moiety that binds to a glucocorticoid receptor. The term "thyroid hormone receptor ligand" as used herein is intended to cover any moiety that binds to a thyroid hormone receptor. The ligand may act as an agonist, an antagonist, a partial agonist, or a partial antagonist.

The term "aliphatic hydrocarbon(s) as used herein refers to acyclic straight or branched chain groups which include alkyl, alkenyl, or alkynyl groups.

The term "aromatic" hydrocarbons(s) as used herein refers to groups including aryl groups as defined herein.

The term "aryl" as employed herein alone or as part of another group refers to monocylcic and bicyclic aromatic groups containing 6 to 10 carbons in the ring portion (such as phenyl or napthyl including 1-naphthyl and 2-naphthyl) and may be optionally substituted through available carbon atoms with 1, 2, or 3 groups selected from hydrogen, halo, alkyl, haloalkyl, alkoxy, haloalkoxy, alkenyl, trifluoromethyl, thiomethyl, difluoromethyloxy trifluoromethyloxy, thiotrifluoromethyl, alkynyl, hydroxy, nitro, or cyano.

Unless otherwise indicated, the term "lower alkenyl" or "alkenyl" as used herein by itself or as part of another group refers to straight or branched chain radicals of 2 to 12 carbons, preferably 2 to 5 carbons, in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, and the like.

Unless otherwise indicated, the term "lower alkynyl" or "alkynyl" as used herein by itself or as part of another group refers to straight or branched chain radicals of 2 to 12 carbons, preferably 2 to 8 carbons, in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4heptynyl, 3-octynyl, 3-nonynyl, 4-decynyl, 3-undecynyl, 4-dodecynyl and the like.

The term "halogen" or "halo" as used herein alone or as part of another group refers to chlorine, bromine, fluorine, and iodine as well as CF3, with chlorine or bromine being preferred.

The term "amino" as employed herein alone or as part of another group may optionally be independently substituted with one or two substituents, which may be the same or different, such as alkyl, aryl, arylalkyl, hydroxyaryl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid or any of the substituents for alkyl as set out above. In addition, the amino substituents may be taken together with the nitrogen atom to which they are attached to form 1pyrrolidinyl, 1piperidinyl, 1azepinyl, 4morpholinyl, 4thiamorpholinyl, 1piperazinyl, 4alkyl1piperazinyl, 4arylalkyl1piperazinyl, 4diarylalkyl1piperazinyl, 1pyrrolidinyl, 1piperidinyl, or 1azepinyl, optionally substituted with alkyl, alkoxy, alkylthio, halo, trifluoromethyl or hydroxy.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1–C4)alkyl or arylsulfonic acids which are unsubstituted or substituted, for example by halogen, for example methane- or ptoluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or trilower alkylamine, for example ethyl, tertbutyl, diethyl, diisopropyl, triethyl, tributyl or dimethyl-propylamine, or a mono, di or trihydroxy lower alkylamine, for example mono di or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I which include a basic group include monohydrochloride, hydrogensulfate, methanesulfonate, phosphate or nitrate.

Preferred salts of the compounds of formula I which include an acid group include sodium, potassium and magnesium salts and pharmaceutically acceptable organic amines.

Preferred are compounds of the invention of formula I wherein:

$R_1$ is carboxylic acid (COOH) or esters thereof, OH, CN, or halogen.

$R_2$ and $R_3$ are halogen such as bromo or chloro; or $R_2$ and $R_3$ are each isopropyl or one is isopropyl and the other is ethyl or tert-butyl.

$R_4$ is aryl.

$R_5$ is isopropyl.

X is a carbonyl (C=O) or methylene (CH$_2$).

Y is hydroxyl or methoxy.

n is 0–4.

Especially preferred compounds of the invention have the structures

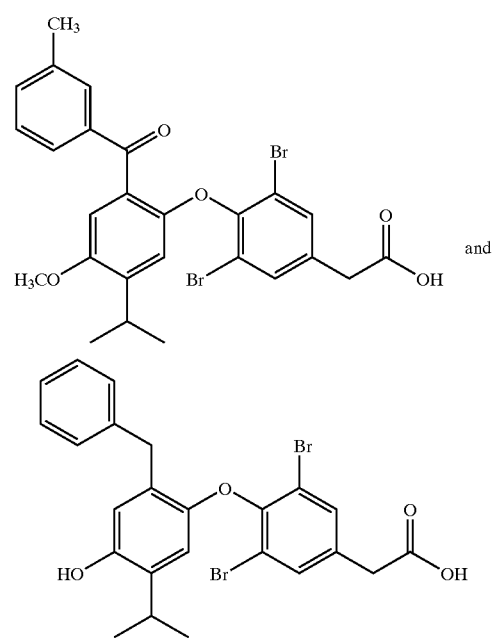

and

The compounds of formula I may be prepared by the processes exemplified in the following reaction schemes. Examples of reagents and procedures for these reactions appear hereinafter and in the working Examples.

Compounds of formula I of the invention can be prepared using the sequence of steps outlined in Scheme 1 or 2 set out below.

Scheme 1

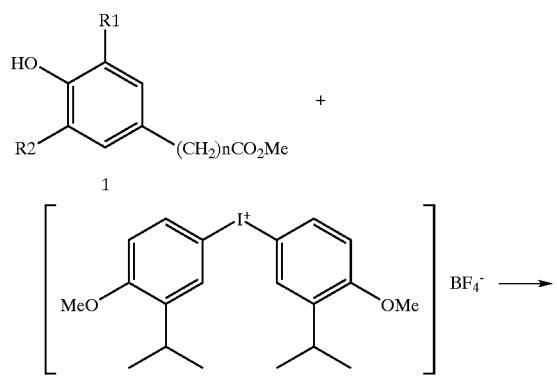

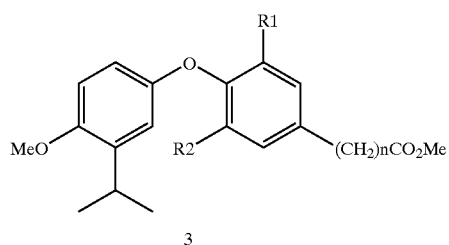

3

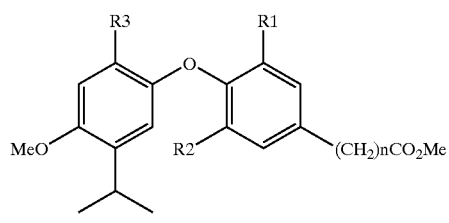

4

Examples 1–4

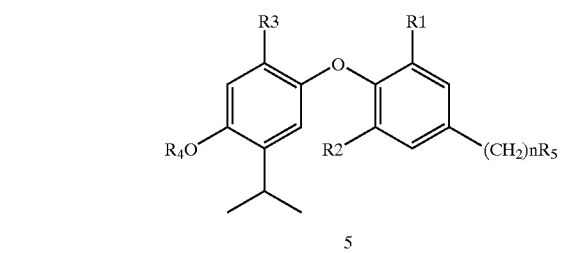

5

Examples 5–47

Scheme 2

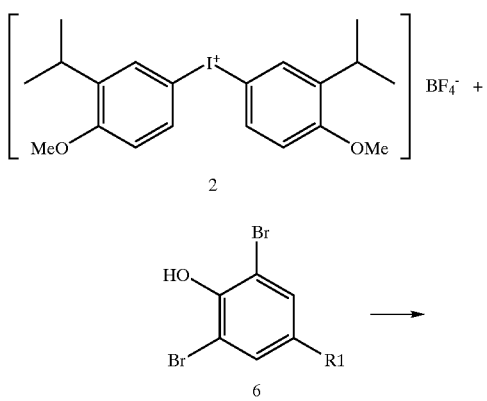

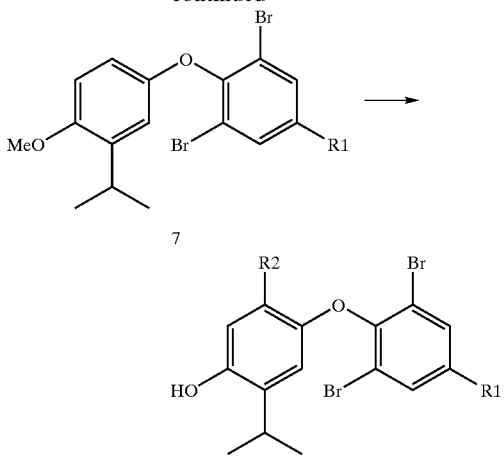

7

8

Examples 48–55

The compounds of the invention are glucocorticoid receptor antagonists or thyroid receptor agonists that are preferably liver selective, and as such are useful in the treatment of diabetes (alone or in combination with agents that stimulate insulin release such as sulfonylureas, influence liver glucose production such as metformin, affect the sensitivity to insulin such as troglitazone, or inhibit glucose absorption such as β-glucosidase inhibitors), obesity, hypercholesterolemia and atherosclerosis by lowering of serum LDL levels (alone or in combination with a cholesterol-lowering drug such as an HMG CoA reductase inhibitor).

The compounds of the invention can be administered orally or parenterally such as subcutaneously or intravenously, as well as by nasal application, rectally or sublingually to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension or in other type carrier materials such as transdermal devices, iontophoretic devices, rectal suppositories, inhalant devices and the like. Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be dministered orally, parenterally, by inhalation spray, topically, rectally, nasally, buccally, vaginally or via an implanted reservoir. The pharmaceutical compositions of this invention may contain any conventional non-toxic pharmaceutically-acceptable carriers, adjuvants or vehicles. The term parenteral as used herein includes subcutaneous, intracutaneous, intrave-nous, intramuscular, intra-articular, intrasynovial, intrasternal, intrathecal, intralesional and intracranial injec-tion or infusion techniques.

The pharmaceutical compositions may be in the form of a sterile injectable preparation, for example, as a sterile injectable aqueous or oleaginous suspension. This suspen-sion may be formulated according to techniques known in the art using suitable dispersing or wetting agents (such as, for example, Tween 80) and suspending agents. The sterile injectable preparation may also be a sterile injectable solu-tion or suspension in a non-toxic parenterally-acceptable diluent or solvent, for example, as a solution in 1,3-butanediol. Among the ac-ceptable vehicles and solvents that may be employed are mannitol, water, Ringer's solution and isotonic sodium chloride solution. In addition, sterile, fixed oils are conven-tionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharma-ceutical-ly-acceptable oils, such as olive oil or cas-tor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspen-sions and solutions. In the case of tablets for oral use, carriers which are commonly used include lactose and corn starch. Lubricating agents, such as magnesium stea-rate, are also typically added. For oral administration in a capsule form, useful diluents include lactose and dried corn starch. When aqueous suspensions are administered orally, the active ingredient is combined with emulsify-ing and sus-pending agents. If desired, certain sweetening and/or flavor-ing and/or coloring agents may be added.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combina-tion, the severity and course of the disease, the patient's disposition to the disease and the judgment of the treating physician. The composition or carrier will contain about 5 to about 500 mg per unit of dosage of a compound of formula I. They may be com-pounded in conventional matter with a physiologically-acceptable vehicle or carrier, excipient, binder, preservative, stabilizer, flavor, etc., as called for by accepted pharmaceu-tical practice.

The following working Examples represent preferred embodiments of the present invention.

EXAMPLE 1

4-(2-Benzoyl-4-hydroxy-5-isopropyl-phenoxy)-3,5-dibromo-benzoic Acid Methyl Ester (Structure 4 of Scheme 1, where $R_1=R_2$=Br, $R_3$=Benzoyl, n=0)

(a) bis(3-isopropyl-4-methoxy-phenyl)iodonium tet-rafluoro borate (structure 2 of scheme 1). Fuming nitric acid (24.8 ml, 530 mmol) was added dropwise to 62.8 ml of acetic acid anhydride cooled in a dry ice/CCl$_4$ bath. Iodine (22.6 g, 88.8 mmol) was added in one portion followed by dropwise addition of trifluoroacetic acid (41 ml, 532 mmol). The reaction mixture was stirred at room temperature until the iodine was dissolved and then purged with $N_2$ to remove nitrogen oxides. The reaction mixture was evaporated, the residue was dissolved in acetic anhydride (252 ml) and cooled in a dry ice/CCl$_4$ bath. To the stirred solution 2-isopropylanisole (80 g, 530 mmol) in acetic anhydride (300 ml) and trifluoroacetic acid (45.2 ml) was added dropwise. The reaction mixture was left at room temperature overnight and then concentrated. The residue was taken up in MeOH (300 ml) and treated with 10% aqueous NaHSO$_3$ (300 ml) and 2M aqueous NaBF$_4$ (2 1). After the precipitate had aggregated, petroleum ether was added and the super-natant was decanted. The precipitate was triturated with petroleum ether, filtered, washed with petroleum ether and dried at room temperature under vacuum to afford 65 g (71%) bis(3-isopropyl-4-methoxyphenyl)iodonium tet-rafluoroborate. (Naokata Yokoyama, Gordon N. Walker, Alan J. Main, James L. Stanton, Michael M. Morrissey, Charles Boehm, Allan Engle, Alan D. Neubert, Jong M. Wasyary, Zouhair F. Stephan and Ronald E. Steele, *J. Med. Chem.*, 38, 695, (1995)).

(b) 3,5-dibromo-4-(3-isopropyl-4-methoxy-phenoxy) benzoic acid methyl ester (structure 3 of scheme 1). To bis(3-isopropyl-4-methoxy-phenyl)iodonium tetrafluorobo-rate (13 g, 25.5 mmol) and copper bronze (2.14 g, 33.7 mmol) in CH$_2$Cl$_2$ (40 ml) at 0° C. was added dropwise a solution of 3,5-dibromo-4-hydroxy-benzoic acid methyl ester (5.3 g, 17.0 mmol) and triethylamine (1.89 g, 18.7 mmol) in CH$_2$Cl$_2$ (26 ml). The reaction mixture was stirred in the dark for 4d and then filtered through celite. The filtrate was evaporated and the residue was purified on silica gel (98:2, petroleum ether/EtOAc) to give 5.96 g (76%) 3,5-dibromo-4-(3-isopropyl-4-methoxy-phenoxy)benzoic acid methyl ester.

(c) 4-(2-benzoyl-5-isopropyl-4-methoxyphenoxy)-3,5-dibromo-benzoic acid methyl ester (structure 3 of scheme 1). To 3,5-dibromo-4-(3-isopropyl-4-methoxy-phenoxy) benzoic acid methyl ester (500 mg, 1.1 mmol) and benzoyl chloride (380 mg, 2.7 mmol) dissolved in CH$_2$Cl$_2$ (10 ml) under nitrogen was added TiCl$_4$ (1.03 g, 5.46 mmol). The mixture was stirred for 2 d at room temperature, poured into ice water and stirred for 2 h. The aqueous phase was extracted with EtOAc. The combined organic layers were washed with 5% sodium carbonate, dried over MgSO$_4$, filtered and concentrated. The crude product was purified on silica (98:2, petroleum ether/EtOAc). 227 mg (37%) of the compound was obtained. $^1$H NMR (CDCl$_3$): d 8.19 (s, 2H), 8.01 (m, 2H), 7.57–7.41 (m, 3H), 7.00 (s, 1H), 6.23 (s, 1H), 3.91 (s, 3H), 3.82 (s, 3H), 3.25 (m, 1H), 1.05 (d, 6H).

EXAMPLE 2

(4-(2-Benzoyl-5-isopropyl-4-methoxy-phenoxy)-3,5-dibromo-phenyl)-acetic Acid Methyl Ester (Structure 4 of Scheme 1, where $R_1=R_2$=Br, $R_3$= Benzoyl, n=1)

(a) (3,5-Dibromo-4-(5-isopropyl-4-methoxy-phenoxy)-phenyl)-acetic acid methyl ester (structure 3 of scheme 1). The compound was prepared by the method described in example 1b from Bis(3-isopropyl-4-methoxyphenyl) iodonium tetrafluoroborate (47.4 g, 92.6 mmol) and 3,5-dibromo-4-hydroxy-phenyl acetic acid methyl ester (20.0 g, 61.7 mmol). The crude product was purified by fractional recrystallization from ether to give 10.7 g (36.7%) of the compound.

(b) (4-(2-Benzoyl-5-isopropyl-4-methoxy-phenoxy)-3,5-Dibromo-phenyl)-acetic acid methyl ester. The compound was prepared by the method described in example 1c from (4-(5-isopropyl-4-methoxy-phenoxy)-3,5-dibromo-phenyl)-acetic acid methyl ester (300 mg, 0.64 mmol) and benzoyl chloride (268 mg, 3.18 mmol). 258 mg (70%) (4-(2-Benzoyl-5-isopropyl-4-methoxy-phenoxy)-3,5-Dibromo-phenyl)-acetic acid methyl ester was obtained. $^1$H NMR (CDCl$_3$): d 8.01 (m, 3H), 7.58–7.38 (m, 4H), 7.00 (s, 1H), 6.26 (s, 1H), 3.82 (s, 3H), 3.69 (s, 3H), 3.54 (s, 2H), 3.24 (m, 1H), 1.09 (d, 6H).

EXAMPLE 3

4-(2-Benzoyl-5-isopropyl-4-methoxy-phenoxy)-3,5-dimethyl-benzoic Acid Methyl Ester (Structure 4 of Scheme 1, where $R_1=R_2$=Me, $R_3$=Benzoyl, n=0)

(a) 4-(5-isopropyl-4-methoxy-phenoxy)-3,5-dimethyl-benzoic acid methyl ester (structure 3 of scheme 1). The compound was prepared by the method described in example 1b from bis(3-isopropyl-4-methoxyphenyl) iodonium tetrafluoroborate (22.1 g, 43.3 mmol) and 3,5-dimethyl-4-hydroxy-benzoic acid methyl ester (5.20 g, 28.9 mmol). The crude product was purified on silica (97:3 petroleum ether/EtOAc) to give 8.32 g (87%) of the compound.

(b) 4-(2-Benzoyl-5-isopropyl-4-methoxy-phenoxy)-3,5-dimethyl-benzoic acid methyl ester. This compound was prepared by the method described in example 1c from 4-(3-isopropyl-4-methoxy-phenoxy)-3,5-dimethyl-benzoic acid methyl ester (191 mg, 0.58 mmol) and benzoyl chloride (408 mg, 2.9 mmol). 134 mg (53%) of the compound was obtained. $^1$H NMR (CDCl$_3$): d 7.94 (m, 2H), 7.71(s, 2H), 7.54 (m, 1H), 7.45 (m, 2H), 6.96 (s, 1H), 6.19 (s, 1H), 3.88 (s, 3H), 3.80 (s, 3H), 3.22 (m, 1H), 2.04 (s, 6H), 1.00 (d, 6H).

EXAMPLE 4

(4-(2-(4-Chlorophenylacetyl)-5-isopropyl-4-methoxy-phenoxy)-3,5-dibromo-phenyl)-acetic Acid Methyl Ester (Structure 4 of Scheme 1, where $R_1=R_2$=Br, $R_3$=4-Chlorophenylacetyl, n=1)

The compound was prepared by the method described in example 1c from (4-(5-isopropyl-4-methoxy-phenoxy)-3,5-dibromo-phenyl)-acetic acid methyl ester (1.00 g, 2.1 mmol) and 4-chlorophenylacetyl chloride (1.00 g, 5.29 mmol). 208 mg (16%) of the compound was obtained. $^1$H NMR (CD$_3$COCD$_3$) d 7.58 (s, 2H), 7.45–7.16 (m, 5H), 6.23 (s, 1H), 4.49 (s, 2H), 3.80 (s, 3H), 3.73 (s, 3H), 3.62 (s, 2H), 3.18 (m, 1H), 1.03 (d, 6H).

EXAMPLE 5

4-(2-Benzoyl-4-hydroxy-5-isopropyl-phenoxy)-3,5-dibromo-benzoic Acid Methyl Ester (Structure 5 of Scheme 1, where $R_1=R_2$=Br, $R_3$=Benzoyl, $R_4$=H, $R_5=CO_2$Me, n=0)

4-(2-Benzoyl-5-isopropyl-4-methoxy-phenoxy)-3,5-dibromo-benzoic acid methyl ester (210 mg, 0.37 mmol) was dissolved in CH$_2$Cl$_2$ (5 ml) under N$_2$ atmosphere and cooled to −40° C. To the stirred solution, 1M BBr$_3$ (0.75 mmol, 0.75 ml) was added dropwise. The reaction mixture was allowed to reach room temperature and then left overnight. It was cooled to 0° C. and quenched with water (3 ml). The reaction mixture was concentrated and the aqueous phase was extracted with EtOAc. The organic phase was washed with 1M HCl and brine, dried over MgSO$_4$, filtered and concentrated. The crude product was purified on silica (98:2, petroleum ether/EtOAc) to give 73 mg (37%) of the compound. $^1$H NMR (CDCl$_3$): d 8.18 (s, 2H), 7.97–8.03 (m, 2H), 7.41–7.60 (s, 3H), 6.95 (s, 1H), 6.20 (s, 1H), 4.90 (s, 1H), 3.91 (s, 3H), 3.16 (m, 1H), 1.11 (d, 6H,).

EXAMPLE 6

(4-(2-Benzoyl-4-hydroxy-5-isopropyl-phenoxy)-3,5-dibromo-phenyl)-acetic Acid Methyl Ester (Structure 5 of Scheme 1, where $R_1=R_2$=Br, $R_3$=Benzoyl, $R_4$=H, $R_5=CO_2$Me, n=1)

(4-(2-Benzoyl-5-isopropyl-4-methoxy-phenoxy)-3,5-dibromo-phenyl)-acetic acid methyl ester (100 mg, 0.17 mmol) in 5 ml CH$_2$Cl$_2$ was cooled to −20° C. BBr$_3$ (0.52 ml, 3 eq) was added dropwise and the reaction was allowed to reach room temperature and then poured into ice. The two phases were separated and the water phase extracted with CH$_2$Cl$_2$. The combined organic phases were dried over MgSO$_4$ and concentrated. Purification on silica gel gave 69mg (71%) (4-(2-Benzoyl-5-isopropyl-4-hydroxy-phenoxy)-3,5-dibromo-phenyl)-acetic acid methyl ester as a white solid. $^1$H NMR (CD$_3$COCD3): d 8.46 (s, 1H), 7.95 (d, 2H), 7.64 (s, 2H), 7.54 (m, 3H), 7.01 (s, 1H), 6.29 (s, 1H), 3.73 (s, 2H), 3.65 (s, 3H), 3.27 (m, 1H), 1.09 (d, 6H).

EXAMPLE 7

4-(2-Benzoyl-4-hydroxy-5-isopropylphenoxy)-3,5-dibromo-benzoic Acid (Structure 5 of Scheme 1, where $R_1=R_2$=Br, $R_3$=Benzoyl, $R_4$=H, $R_5=CO_2$H, n=0)

4-(2-benzoyl-4-hydroxy-5-isopropylphenoxy)-3,5-dibromo-benzoic acid methyl ester was treated with 1M NaOH in acetone. $^1$H NMR (CD$_3$COCD$_3$) d 8.22 (s, 2H), 7.92–8.00 (m, 2H), 7.48–7.68 (s, 3H), 7.02 (s, 1H), 6.35 (s, 1H), 3.18 (m, 1H), 1.09 (d, 6H).

EXAMPLE 8

(4-(2-Benzoyl-4-hydroxy-5-isopropyl-phenoxy)-3,5-dibromo-phenyl)-acetic Acid (Structure 5 of Scheme 1, where $R_1=R_2$=Br, $R_3$=Benzoyl, $R_4$=H, $R_5=CO_2$H, n=1)

This compound was prepared by a similar method described for example 5 from (4-(2-benzoyl-5-isopropyl-4-methoxy-phenoxy)-3,5-dibromo-phenyl)-acetic acid methyl ester (100 mg, 0.17 mmol) to afford 69 mg (71%) (4-(2-benzoyl-4-hydroxy-5-isopropyl-phenoxy)-3,5-dibromo-phenyl)-acetic acid. $^1$H NMR (CD$_3$COCD$_3$): d 8.46 (s, 1H), 7.95 (d, 2H), 7.64 (s, 2H), 7.54 (m, 3H), 7.01 (s, 1H), 6.29 (s, 6.29), 3.73 (s, 2H), 3.65 (s, 3H), 3.27 (m, 1H), 1.09 (d, 6H).

EXAMPLE 9

(4-(3-Benzyl-4-hydroxy-5-isopropyl-phenoxy)-3,5-dibromo-phenyl)-acetic Acid (Structure 5 of Scheme 1, where $R_1=R_2$=Br, $R_3$=Benzyl, $R_4$=H, $R_5=CO_2$H, n=1)

(a) (4-(3-Benzyl-5-isopropyl-4-methoxy-phenoxy)-3,5-dibromo-phenyl)-acetic acid methyl ester. To (4-(3-Benzoyl-5-isopropyl-4-methoxy-phenoxy)-3,5-dibromo-phenyl)-acetic acid methyl ester, hydrazine hydrate, potassium carbonate and diethylene glycol were added. The solution was heated to 150° C. overnight and then to 200° C. for 4 hours. The reaction mixture was diluted with water, extracted with ethyl acetate, dried over $MgSO_4$, filtered and evaporated. The crude product was purified on silica to afford (4-(3-benzyl-4-metoxy-5-isopropyl-phenoxy)-3,5-dibromo-phenyl)-acetic acid methyl ester.

(b) (4-(3-Benzyl-4-hydroxy-5-isopropyl-phenoxy)-3,5-dibromo-phenyl)-acetic acid. This compound was prepared by the method described for example 5 from (4-(3-Benzyl-5-isopropyl-4-methoxy-phenoxy)-3,5-dibromo-phenyl)-acetic acid methyl ester. $^1$H NMR ($CD_3COCD_3$): d 7.95 (s, 1H) , 7.72 (s, 2H), 7.34–7.11 (m, 5H), 6.61 (s, 1H), 6.15 (s, 1H), 4.09 (s, 2H), 3.74 (s, 2H), 3.14 (m, 1H), 1.00 (d, 6H).

EXAMPLE 10

(3,5-Dibromo-4-(4-hydroxy-5-isopropyl-2-(2-naphtoyl-benzoyl)-phenoxy)-phenyl)-acetic Acid (Structure 5 of Scheme 1, where $R_1=R_2=Br$, $R_3=2$-Naphthoyl, $R_4=H$, $R_5=CO_2H$, n=1)

(a) (3,5-Dibromo-4-(4-hydroxy-5-isopropyl-2-(2-naphtoyl-benzoyl)-phenoxy)-phenyl)-acetic acid methyl ester This compound was prepared by the method described in example 1c from (4-(5-isopropyl-4-methoxy-phenoxy)-3,5-dibromo-phenyl)-acetic acid methyl ester (2.00 g, 3.98 mmol) and 2-naphthoylchloride (1.89 g, 9.95 mmol). 1200 mg (48%) of the compound was obtained as a solid.

(b) (3,5-Dibromo-4-(4-hydroxy-5-isopropyl-2-(2-naphthoyl-benzoyl)-phenoxy)-phenyl)-acetic acid. This compound was prepared by a similar method described for example 5 from (3,5-dibromo-4-(4-hydroxy-5-isopropyl-2-(2-naphtoyl-benzoyl)-phenoxy)-phenyl)-acetic acid methyl ester (304 mg, 0.49 mmol) to afford 141 mg (49%) 4-(4-hydroxy-5-isopropyl-2-(2-naphthoyl)phenoxy)-3,5-dibromo-acetic acid. $^1$H NMR ($CD_3SOCD_3$): d 1.04 (d, 6H, $CH_3$), 3.18 (m, 1H, CH), 3.62 (s, 2H, $CH_2$), 6.18 (s, 1H), 7.00 (s, 1H), 7.52–7.71 (m, 4H), 7.96–8.19 (m, 4H), 8.49 (s, 1H), 9.52 (s, 1H), 12.49 (s, 1H).

EXAMPLE 11

(3,5-Dibromo-4-(4-hydroxy-5-isopropyl-2-(4-tert-butyl-benzoyl)-phenoxy)-phenyl)-acetic Acid. (Structure 5 of Scheme 1, where $R_1=R_2=Br$, $R_3=4$-tert-Butyl-benzoyl, $R_4=H$, $R_5=CO_2H$, n=1)

(a) 3,5-Dibromo-4-(4-hydroxy-5-isopropyl-2-(4-tert-butyl-benzoyl)-phenoxy)-phenyl)-acetic acid methyl ester. This compound was prepared by the method described in example 1c from (4-(5-isopropyl-4-methoxy-phenoxy)-3,5-dibromo-phenyl)-acetic acid methyl ester (2.0 g, 4.23 mmol) and 4-tert-butylbenzoyl chloride (2.1 g, 10.6 mmol) to give 2100 mg (78%) 3,5-dibromo-4-(4-hydroxy-5-isopropyl-2-(4-tert-butyl-benzoyl)-phenoxy)-phenyl)-acetic acid methyl ester.

(b) 3,5-Dibromo-4-(4-hydroxy-5-isopropyl-2-(4-tert-butyl-benzoyl)-phenoxy)-phenyl)-acetic acid. This compound was prepared by a similar method described for example 5 from 3,5-dibromo-4-(4-hydroxy-5-isopropyl-2-(4-tert-butyl-benzoyl)-phenoxy)-phenyl)-acetic acid methyl ester (500 mg, 0.79 mmol) to afford 461 mg (96%) 3,5-dibromo-4-(4-hydroxy-5-isopropyl-2-(4-tert-butyl-benzoyl)-phenoxy)-phenyl)-acetic acid. $^1$H NMR ($CD_3COCD_3$): d 1.06 (d, 6H, $CH_3$), 1.33 (s, 9H), 3.21 (m, 1H, CH), 3.91 (s, 3H, $CH_3$), 6.23 (s, 1H), 6.86 (s, 1H), 7.49–7.62 (m, 4H), 7.86–7.93 (m, 2H).

EXAMPLE 12

(4-(2-Benzoyl-5-isopropyl-4-methoxy-phenoxy)-3,5-dibromo-phenyl)-acetic Acid (Structure 5 of Scheme 1, where $R_1=R_2=Br$, $R_3=Benzoyl$, $R_4=Me$, $R_5=CO_2H$, n=1)

(4-(2-Benzoyl-4-hydroxy-5-isopropyl-phenoxy)-3,5-dibromo-phenyl)-acetic acid methyl ester (100 mg, 0.17 mmol) was dissolved in a 3:5 mixture of 1 M NaOH/MeOH (2.5 ml). The reaction was stirred at room temperature over night and then acidified with 1M HCl. The solvents were evaporated and the aqueous phase extracted with EtOAc. The combined organic phases were dried over $MgSO_4$, evaporated and the residue dried under vacuum. 82 mg (84%) of the compound was obtained as a white solid. $^1$H NMR ($CD_3COCD_3$): d 7.97 (m, 2H) , 7.66 (s, 2H) , 7.55 (m, 3H), 7.09 (s, 1H), 6.33 (s, 1H), 3.87 (s, 3H), 3.64 (s, 2H), 3.26 (m, 1H), 1.07 (d, 6H).

EXAMPLE 13

2-(3,5-Dibromo-4-(2-(hydroxy-phenyl-methyl)-5-isopropyl-4-methoxy-phenoxy)-phenyl)-ethanol (Structure 5 of Scheme 1, where $R_1=R_2=Br$, $R_3=$Hydroxy-phenyl-methyl, $R_4=Me$, $R_5=CH_2OH$, n=1)

To a solution of (4-(2-benzoyl-5-isopropyl-4-methoxy-phenoxy)-3,5-dibromo-phenyl)-acetic acid methyl ester (100 mg, 0.17 mmol) in THF under $N_2$ atmosphere was added DIBAL (0.87 ml, 5 eq) dropwise at 0° C. The reaction was stirred at 0° C. for 15 minutes and allowed to reach room temperature and stirred for another 2 h. The mixture was poured into ice, and the aqueous phase extracted with EtOAc and the combined organic layers were dried over $MgSO_4$ and concentrated. Purification on silica gave 2-(3,5-dibromo-4-(2-(hydroxy-phenyl-methyl)-5-isopropyl-4-methoxy-phenoxy)-phenyl)-ethanol as a solid (mg, %). $^1$H NMR ($CD_3COCD_3$): d

EXAMPLE 14

2-(4-(2-Benzyl-5-isopropyl-4-methoxy-phenoxy)-3,5-dibromo-phenyl)-ethanol (Structure 5 of Scheme 1, where $R_1=R_2=Br$, $R_3=Benzyl$, $R_4=Me$, $R_5=CH_2OH$, n=1)

(a) (4-(2-Benzyl-5-isopropyl-4-methoxy-phenoxy)-3,5-dibromo-phenyl)-acetic acid methyl ester. To a mixture of (4-(2-Benzoyl-5-isopropyl-4-methoxy-phenoxy)-3,5-dibromo-phenyl)-acetic acid methyl ester (50 mg, 0.09 mmol) and $CF_3COOH$ (0.260) ml in $CH_2Cl_2$ (0.350 ml) at 0° C. was added $NaBH_4$ (21 mg, 6 eq). The reaction was stirred at 0° C. for 30 min and then at room temperature for 1 h. The mixture was poured into ice and neutralized with saturated $NaHCO_3$ (aq). The aqueous phase was extracted with EtOAc and the combined organic phases were washed with water and dried over $MgSO_4$. Evaporation under diminished pressure gave 49 mg (99%). (4-(2-benzyl-5-isopropyl-4-methoxy-phenoxy)-3,5-dibromo-phenyl)-acetic acid methyl ester as a white solid.

(b) 2-(4-(2-Benzyl-5-isopropyl-4-methoxy-phenoxy)-3,5-dibromo-phenyl)-ethanol. The compound was prepared by the procedure in example 13 from (4-(2-Benzyl-5-isopropyl-4-methoxy-phenoxy)-3,5-dibromo-phenyl)-acetic acid methyl ester. $^1$H NMR ($CDCl_3$): d 7.47 (s, 2H) , 7.26 (m, 5H) , 6.63 (s, 1H) , 6.14 (s, 1H), 4.18 (s, 2H), 3.90 (t, 2H), 3.70 (s, 3H), 3.15 (m, 1H), 2.84 (t, 2H), 1.03 (d, 6H).

EXAMPLE 15

(4-(2-Benzyl-5-isopropyl-4-methoxy-phenoxy)-phenyl)-acetic Acid (Structure 5 of Scheme 1, where $R_1=R_2=H$, $R_3=Benzyl$, $R_4=Me$, $R_5=CO_2H$, n=1)

(a) (4-(3-Benzyl-5-isopropyl-4-methoxy-phenoxy)-phenyl)-acetic acid methyl ester. A solution of (4-(2-

Benzoyl-4-hydroxy-5-isopropyl-phenoxy)-3,5-dibromo-phenyl)-acetic acid methyl ester (100 mg, 0.17 mmol) in methanol (4 ml) was stirred under an atmosphere of hydrogen with Pd—C 10% (10 mg) at room temperature for 16 h. Filtration and purification on silica (EtOAc/n-heptane 1:9) gave (4-(3-benzyl-5-isopropyl-4-methoxy-phenoxy)-phenyl)-acetic acid methyl ester (54.7 mg, 78%) as a white solid.

(b) (4-(3-Benzyl-5-isopropyl-4-methoxy-phenoxy)-phenyl)-acetic acid. This compound was prepared by the method described for example 12 from (4-(3-Benzyl-5-isopropyl-4-methoxy-phenoxy)-3,5-dibromo-phenyl)-acetic acid methyl ester (20 mg, 0.05 mmol) to afford 18.5 mg (96%) of the compound. $^1$H NMR (CDCl$_3$): d 7.22–7.13 (m, 7H), 6.84 (s, 1H), 6.77 (m, 2H), 6.62 (s, 1H), 3.83 (s, 2H), 3.73 (s, 3H), 3.59 (s, 2H), 3.22 (m, 1H), 1.11 (d, 6H).

EXAMPLE 16

4-(2-Benzoyl-5-isopropyl-4-methoxy-phenoxy)-3,5-dimethyl-benzoic Acid (Structure 5 of Scheme 1, where $R_1=R_2=Me$, $R_3=Benzoyl$, $R_4=Me$, $R_5=CO_2H$, n=0)

This compound was prepared by the method described for example 12 from 4-(2-benzoyl-5-isopropyl-4-methoxy-phenoxy)-3,5-dimethyl-benzoic acid methyl ester (50 mg, 0.12 mmol). 39 mg (81%) of the compound was obtained as a white solid. $^1$H NMR (CD$_3$CN): d 7.92 (m, 2H), 7.74 (s, 2H), 7.69–7.52 (m, 3H), 3.86 (s, 3H), 3.24 (m, 1H), 2.09 (s, 6H), 1.02 (d, 6H).

EXAMPLE 17

4-(2-Benzoyl-5-isopropyl-4-methoxy-phenoxy)-3,5-diisopropyl-benzoic Acid (Structure 5 of Scheme 1, where $R_1=R_2=Isopropyl$, $R_3=Benzoyl$, $R_4=Me$, $R_5=CO_2H$, n=0)

(a) 4-(5-Isopropyl-4-methoxy-phenoxy)-3,5-diisopropyl-benzoic acid methyl ester. This compound was prepared by the method described in example 1b from bis(3-isopropyl-4-methoxyphenyl)iodonium tetrafluoroborate (814 mg, 1.59 mmol) and 3,5-diisopropyl-4-hydroxy-phenyl benzoic acid methyl ester (250 mg, 1.06 mmol) to afford 297 mg (73%) of the compound.

(b) 4-(2-Benzoyl-5-isopropyl-4-methoxy-phenoxy)-3,5-diisopropyl-benzoic acid methyl ester. The compound was prepared by the method described in example 1c from 4-(5-isopropyl-4-methoxy-phenoxy)-3,5-diisopropyl-benzoic acid methyl ester (28 mg, 0.073 mmol) and benzoyl chloride (51 mg, 0.36 mmol). 23.5 mg (66%) of the compound was obtained as a white solid.

(c) 4-(2-benzoyl-5-isopropyl-4-methoxy-phenoxy)-3,5-diisopropyl-benzoic acid. This compound was prepared by the method described for example 12 from 4-(2-Benzoyl-5-isopropyl-4-methoxy-phenoxy)-3,5-diisopropyl-benzoic acid methyl ester (16 mg, 0.12 mmol). 11 mg (71%) of the compound was obtained as a white solid. $^1$H NMR (CDCl$_3$): d 7.92 (m, 2H), 7.88 (s, 2H), 7.54 (m, 1H), 7.44 (m, 2H), 6.99 (s, 1H), 6.17 (s, 1H), 3.82 (s, 3H), 3.24 (m, 1H), 2.95 (m, 2H), 1.10 (d, 6H), 0.98 (d, 12H).

EXAMPLE 18

(3,5-Dibromo-4-(2-(2-fluoro-benzoyl)-5-isopropyl-4-methoxy-phenoxy)-phenyl)-acetic Acid (Structure 5 of Scheme 1, where $R_1=R_2=Br$, $R_3=2$-Fluoro-benzoyl, $R_4=Me$, $R_5=CO_2H$, n=1)

(a) (3,5-Dibromo-4-(2-(2-fluoro-benzoyl)-5-isopropyl-4-methoxy-phenoxy)-phenyl)-acetic acid methyl ester. This compound was prepared by the method described in example 1c from (4-(5-isopropyl-4-methoxy-phenoxy)-3,5-dibromo-phenyl)-acetic acid methyl ester (50 mg, 0.11 mmol) and 4-fluro-benzoyl chloride (84 mg, 0.53 mmol). 50 mg (79%) of the compound was obtained as a white solid.

(b) (3,5-Dibromo-4-(2-(2-fluoro-benzoyl)-5-isopropyl-4-methoxy-phenoxy)-phenyl)-acetic acid. This compound was prepared by the method described for example 12 from (3,5-dibromo-4-(2-(2-fluoro-benzoyl)-5-isopropyl-4-methoxy- phenoxy)-phenyl)-acetic acid methyl ester (25 mg, 0.04 mmol) to afford 19 mg (78%) of the compound. $^1$H NMR (CDCl$_3$): d 7.69 (m, 1H), 7.48–7.35 (m, 3H), 7.23 (s, 1H), 7.16 (m, 1H), 7.05 (m, 1H), 6.19 (m, 1H), 3.86 (s, 3H), 3.58 (s, 2H), 3.22 (m, 1H), 1.04 (d, 6H).

EXAMPLE 19

(3,5-Dibromo-4-(2-(3-fluoro-benzoyl)-5-isopropyl-4-methoxy-phenoxy)-phenyl)-acetic Acid (Structure 5 of Scheme 1, where $R_1=R_2=Br$, $R_3=3$-Fluoro-benzoyl, $R_4=Me$, $R_5=CO_2H$, n=1)

(a) (3,5-Dibromo-4-(2-(3-fluoro-benzoyl)-5-isopropyl-4-methoxy-phenoxy)-phenyl)-acetic acid methyl ester. This compound was prepared by the method described in example 1c from (4-(5-isopropyl-4-methoxy-phenoxy)-3,5-dibromo-phenyl)-acetic acid methyl ester (50 mg, 0.11 mmol) and 3-fluorobenzoyl chloride (84 mg, 0.53 mmol). 52 mg (83%) of the compound was obtained as a white solid.

(b) (3,5-Dibromo-4-(2-(3-fluoro-benzoyl)-5-isopropyl-4-methoxy-phenoxy)-phenyl)-acetic acid. This compound was prepared by the method described for example 12 from (3,5-dibromo-4-(2-(3-fluoro-benzoyl)-5-isopropyl-4-methoxy-phenoxy)-phenyl)-acetic acid methyl ester (25 mg, 0.04 mmol) to afford 18 mg (74%) of the compound. $^1$H NMR (CDCl$_3$): d 7.79 (m, 1H), 7.68 (m, 1H), 7.46 (s, 2H), 7.39 (m, 1H), 7.22 (m, 1H), 7.02 (s, 1H), 6.25 (s, 1H), 3.83 (s, 3H), 3.59 (s, 2H), 3.24 (m, 1H), 1.06 (d, 6H).

EXAMPLE 20

(3,5-Dibromo-4-(2-(4-fluoro-benzoyl)-5-isopropyl-4-methoxy-phenoxy)-phenyl)-acetic Acid (Structure 5 of Scheme 1, where $R_1=R_2=Br$, $R_3=4$-Fluoro-benzoyl, $R_4=Me$, $R_5=CO_2H$, n=1)

(a) (3,5-Dibromo-4-(2-(4-fluoro-benzoyl)-5-isopropyl-4-methoxy-phenoxy)-phenyl)-acetic acid methyl ester. This compound was prepared by the method described in example 1c from (4-(5-isopropyl-4-methoxy-phenoxy)-3,5-dibromo-phenyl)-acetic acid methyl ester (50 mg, 0.11 mmol) and 4-fluorobenzoyl chloride (84 mg, 0.53 mmol). 55 mg (87%) of the compound was obtained as a white solid.

(b) (3,5-Dibromo-4-(2-(4-fluoro-benzoyl)-5-isopropyl-4-methoxy-phenoxy)-phenyl)-acetic acid. This compound was prepared by the method described for example 12 from (3,5-dibromo-4-(2-(4-fluoro-benzoyl)-5-isopropyl-4-methoxy-phenoxy)-phenyl)-acetic acid methyl ester (25 mg, 0.04 mmol) to afford 20 mg (82%) of the compound. $^1$H NMR (CDCl$_3$): d 8.04 (m, 2H), 7.45 (s, 2H), 7.09 (m, 2H), 7.00 (s, 1H), 6.25 (s, 1H), 3.82 (s, 3H), 3.61 (s, 2H), 3.24 (m, 1H) , 1.06 (d, 6H).

EXAMPLE 21

3,5-Dibromo-4-(5-isopropyl-4-methoxy-2-(2-methyl-benzoyl)-phenoxy)-phenyl)-acetic Acid (Structure 5 of Scheme 1, where $R_1=R_2=Br$, $R_3=2$-Methyl-benzoyl, $R_4=Me$, $R_5=CO_2H$, n=1)

(a) 3,5-Dibromo-4-(5-isopropyl-4-methoxy-2-(2-methyl-benzoyl)-phenoxy)-phenyl)-acetic acid methyl ester. This compound was prepared by the method described in example 1c from (4-(5-isopropyl-4-methoxy-phenoxy)-3,5-dibromo-phenyl)-acetic acid methyl ester (50 mg, 0.11 mmol) and 2-methylbenzoyl chloride (82 mg, 0.53 mmol). 48 mg (77%) of the compound was obtained as a white solid.

(b) 3,5-Dibromo-4-(5-isopropyl-4-methoxy-2-(2-methyl-benzoyl)-phenoxy)-phenyl)-acetic acid. This compound was prepared by the method described for example 12 from 3,5-dibromo-4-(5-isopropyl-4-methoxy-2-(2-methyl-benzoyl)-phenoxy)-phenyl)-acetic acid methyl ester (25 mg, 0.04 mmol) to afford 17 mg (71%) of the compound. $^1$H NMR (CDCl$_3$): d 7.50 (m, 1H), 7.41 (s, 2H), 7.19 (m, 3H), 7.18 (s, 1H), 6.14 (s, 1H), 3.82 (s, 3H), 3.56 (s, 2H), 3.21 (m, 1H), 2.50 (s, 3H), 1.05 (d, 6H).

EXAMPLE 22

(3,5-Dibromo-4-(5-isopropyl-4-methoxy-2-(3-methyl-benzoyl)-phenoxy) phenyl)-acetic Acid (Structure 5 of Scheme 1, where $R_1=R_2=Br$, $R_3=3$-Methyl-benzoyl, $R_4=Me$, $R_5=CO_2H$, n=1)

(a) (3,5-Dibromo-4-(5-isopropyl-4-methoxy-2-(3-methyl-benzoyl)-phenoxy) phenyl)-acetic acid methyl ester. This compound was prepared by the method described in example 1c from (4-(5-isopropyl-4-methoxy-phenoxy)-3,5-dibromo-phenyl)-acetic acid methyl ester (50 mg, 0.11 mmol) and 3-methylbenzoyl chloride (82 mg, 0.53 mmol). 52 mg (83%) of the compound was obtained as a yellow solid.

(b) (3,5-Dibromo-4-(5-isopropyl-4-methoxy-2-(3-methyl-benzoyl)-phenoxy) phenyl)-acetic acid. This compound was prepared by the method described for example 12 from 3,5-dibromo-4-(5-isopropyl-4-methoxy-2-(3-methyl-benzoyl)-phenoxy) phenyl)-acetic acid methyl ester (25 mg, 0.04 mmol) to afford 19 mg (80%) of the compound. $^1$H NMR (CDCl$_3$): d 7.80 (m, 2H), 7.42 (s, 2H), 7.33 (m, 2H), 6.98 (s, 1H), 6.24 (s, 1H), 3.80 (s, 3H), 3.57 (s, 2H), 3.22 (m, 1H), 2.37 (s, 3H), 1.07 (d, 6H).

EXAMPLE 23

(3,5-Dibromo-4-(5-isopropyl-4-methoxy-2-(4-methyl-benzoyl)-phenoxy)-phenyl)-acetic Acid (Structure 5 of Scheme 1, where $R_1=R_2=Br$, $R_3=4$-Methyl-benzoyl, $R_4=Me$, $R_5=CO_2H$, n=1)

(a) (3,5-Dibromo-4-(2-(4-methyl-benzoyl)-5-isopropyl-4-methoxy-phenoxy)-phenyl)-acetic acid methyl ester. This compound was prepared by the method described in example 1c from (4-(5-isopropyl-4-methoxy-phenoxy)-3,5-dibromo-phenyl)-acetic acid methyl ester (50 mg, 0.11 mmol) and 4-methylbenzoyl chloride (82 mg, 0.53 mmol). 56 mg (89%) of the compound was obtained as a white solid.

(b) (3,5-Dibromo-4-(5-isopropyl-4-methoxy-2-(4-methyl-benzoyl)-phenoxy)-phenyl)-acetic acid. This compound was prepared by the method described for example 12 from (3,5-dibromo-4-(2-(4-methyl-benzoyl)-5-isopropyl-4-methoxy-phenoxy)-phenyl)-acetic acid methyl ester (25 mg, 0.04 mmol) to afford 22 mg (92%) of the compound. 1H NMR (CDCl$_3$): d 7.89 (m, 2H), 7.43 (s, 2H), 7.23 (m, 2H), 6.96 (s, 1H), 6.24 (s, 1H), 3.79 (s, 3H), 3.57 (s, 2H), 3.22 (m, 1H), 2.38 (s, 3H), 1.04 (d, 6H).

EXAMPLE 24

(3,5-Dibromo-4-(2-(4-diphenylacetoyl)-5-isopropyl-4-methoxy-phenoxy)-phenyl)-acetic Acid (Structure 5 of Scheme 1, where $R_1=R_2=Br$, $R_3=$Diphenylacetyl, $R_4=Me$, $R_5=CO_2H$, n=1)

(a) (3,5-Dibromo-4-(2-(diphenylacetyl)-5-isopropyl-4-methoxy-phenoxy)-phenyl)-acetic acid methyl ester. This compound was prepared by a similar method described for example 9 from (4-(5-isopropyl-4-methoxy-phenoxy)-3,5-dibromo-phenyl)-acetic acid methyl ester (1.00 g, 2.1 mmol) and diphenyl acetyl chloride (1.22 g, 5.29 mmol). 438 mg (32%) of the compound was obtained as a solid.

(b) (3,5-Dibromo-4-(2-(4-diphenylacetyl)-5-isopropyl-4-methoxy-phenoxy)-phenyl)-acetic acid. This compound was prepared by the method described for example 12 from (3,5-dibromo-4-(2-(4-diphenylacetyl)-5-isopropyl-4-methoxy-phenoxy)-phenyl)-acetic acid methyl ester (63 mg, 0.095 mmol) to afford 51 mg (83%) of the compound. $^1$H NMR (CDCl$_3$): d 7.55 (s, 2H), 7.36–7.14 (m, 1H), 6.56 (s, 1H), 6.15 (s, 1H), 3.78 (s, 3H), 3.67 (s, 2H), 3.16 (m, 1H), 2.38 (s, 3H), 1.00 (d, 6H).

EXAMPLE 25

(4-(2-(3-Chloro-benzoyl)-5-isopropyl-4-methoxy-phenoxy)-3,5-dibromo-phenyl)-acetic Acid (Structure 5 of Scheme 1, where $R_1=R_2=Br$, $R_3=3$-Chloro-benzoyl, $R_4=Me$, $R_5=CO_2H$, n=1)

(a) (4-(2-(3-Chloro-benzoyl)-5-isopropyl-4-methoxy-phenoxy)-3,5-dibromo-phenyl)-acetic acid methyl ester. This compound was prepared by the method described in example 1c from (4-(5-isopropyl-4-methoxy-phenoxy)-3,5-dibromo-phenyl)-acetic acid methyl ester (100 mg, 0.21 mmol) and 3-chlorobenzoyl chloride (183 mg, 1.05 mmol). 25 mg (20%) of the compound was obtained as a yellow oil.

(b) (4-(2-(3-Chloro-benzoyl)-5-isopropyl-4-methoxy-phenoxy)-3,5-dibromo-phenyl)-acetic acid. This compound was prepared by a similar method described for example 12 from (4-(2-(3-chloro-benzoyl)-5-isopropyl-4-methoxy-phenoxy)-3,5-dibromo-phenyl)-acetic acid methyl ester (25 mg, 0.041 mmol) to afford 14 mg (57%) of the compound as a yellow solid. $^1$H NMR (CDCl$_3$): d 7.55 (s, 2H), 7.36–7.14 (m, 4H), 6.56 (s, 1H), 6.15 (s, 1H), 3.78 (s, 3H), 3.67 (s, 2H), 3.16 (m, 1H), 2.38 (s, 3H), 1.00 (d, 6H).

EXAMPLE 26

(4-(2-(4-Chloro-benzoyl)-5-isopropyl-4-methoxy-phenoxy)-3,5-dibromo-phenyl)-acetic Acid (Structure 5 of Scheme 1, where $R_1=R_2=Br$, $R_3=4$-Chloro-benzoyl, $R_4=Me$, $R_5=CO_2H$, n=1)

(a) (4-(2-(4-Chloro-benzoyl)-5-isopropyl-4-methoxy-phenoxy)-3,5-dibromo-phenyl)-acetic acid methyl ester. This compound was prepared by the method described in example 1c from (3,5-dibromo-4-(5-isopropyl-4-methoxy-phenoxy)-phenyl)-acetic acid methyl ester (50 mg, 0.11 mmol) and 4-chlorobenzoyl chloride (93 mg, 0.53 mmol) to afford 53 mg (82%) (4-(2-(4-Chloro-benzoyl)-5-isopropyl-4-methoxy-phenoxy)-3,5-dibromo-phenyl)-acetic acid methyl ester as a yellow solid.

(b) (4-(2-(4-Chloro-benzoyl)-5-isopropyl-4-methoxy-phenoxy)-3,5-dibromo-phenyl)-acetic acid methyl ester. This compound was prepared by the method described for example 12 from (4-(2-(4-chloro-benzoyl)-5-isopropyl-4-methoxy-phenoxy)-3,5-dibromo-phenyl)-acetic acid methyl ester (25 mg, 0.04 mmol) to afford 15 mg (61%) of the compound. $^1$H NMR (CDCl$_3$): d 7.78 (m, 4H), 7.46 (s, 1H), 7.01 (s, 1H), 6.25 (s, 1H), 3.82 (s, 3H), 3.60 (s, 2H), 3.24 (m, 1H), 1.08 (d, 6H).

EXAMPLE 27

(4-(2-(3-Bromo-benzoyl)-5-isopropyl-4-methoxy-phenoxy)-3,5-dibromo-phenyl)-acetic Acid (Structure 5 of Scheme 1, where $R_1=R_2=Br$, $R_3=3$-Bromo-benzoyl, $R_4=Me$, $R_5=CO_2H$, n=1)

(a) (4-(2-(3-Bromo-benzoyl)-5-isopropyl-4-methoxy-phenoxy)-3,5-dibromo-phenyl)-acetic acid methyl ester.

This compound was prepared by the method described in example 13 from (3,5-dibromo-4-(5-isopropyl-4-methoxyphenoxy)-phenyl)-acetic acid methyl ester (100 mg, 0.21 mmol) and 3-bromobenzoyl chloride (161 mg, 0.73 mmol) to afford 46 mg (34%) of the compound as a yellow solid.

(b) (3,5-Dibromo-4-(2-(3-bromo-benzoyl)-5-isopropyl-4-methoxy-phenoxy)-phenyl)-acetic acid. This compound was prepared by a similar method described for example 12 from (3,5-Dibromo-4-(2-(3-bromo-benzoyl)-5-isopropyl-4-methoxy-phenoxy)-phenyl)-acetic acid methyl ester (45 mg, 0.07 mmol) to afford 34 mg (78%) of the compound. $^1$H NMR (CDCl$_3$): d 8.09 (m, 1H), 7.92 (m, 1H), 7.64 (m, 1H), 7.31 (m, 1H), 7.03 (s, 1H), 6.24 (s, 1H), 3.83 (s, 3H), 3.60 (s, 2H), 3.24 (m, 1H), 1.08 (d, 6H).

EXAMPLE 28

(3,5-Dibromo-4-(2-(3-iodo-benzoyl)-5-isopropyl-4-methoxy-phenoxy)-phenyl)-acetic Acid (Structure 5 of Scheme 1, where R$_1$=R$_2$=Br, R$_3$=3-Iodo-benzoyl, R$_4$=Me, R$_5$=CO$_2$H, n=1)

(a) (3,5-Dibromo-4-(2-(3-iodo-benzoyl)-5-isopropyl-4-methoxy-phenoxy)-phenyl)-acetic acid methyl ester. This compound was prepared by the method described in example 1c from (3,5-dibromo-4-(5-isopropyl-4-methoxyphenoxy)-phenyl)-acetic acid methyl ester (2.0 g, 4.2 mmol) and 3-iodobenzoyl chloride (3.9 g, 14.7 mmol) to afford 1.27 g (43%) (3,5-dibromo-4-(2-(3-iodo-benzoyl)-5-isopropyl-4-methoxy-phenoxy)-phenyl)-acetic acid methyl ester as a yellow solid.

(b) (3,5-Dibromo-4-(2-(3-iodo-benzoyl)-5-isopropyl-4-methoxy-phenoxy)-phenyl)-acetic acid. This compound was prepared by a similar method described for example 12 from (3,5-dibromo-4-(2-(3-iodo-benzoyl)-5-isopropyl-4-methoxy-phenoxy)-phenyl)-acetic acid methyl ester (500 mg, 0.71 mmol) to afford 472 mg (96%) of the compound. $^1$H NMR (CDCl$_3$): d 8.26 (m, 1H), 7.97 (m, 1H), 7.85 (m, 1H), 7.19 (m, 1H), 7.02 (s, 1H), 6.24 (s, 1H), 3.83 (s, 3H), 3.60 (s, 2H), 3.24 (m, 1H), 1.06 (d, 6H).

EXAMPLE 29

(3,5-Dibromo-4-(2-(4-iodo-benzoyl)-5-isopropyl-4-methoxy-phenoxy)-phenyl)-acetic Acid (Structure 5 of Scheme 1, where R$_1$=R$_2$=Br, R$_3$=4-Iodobenzoyl, R$_4$=Me, R$_5$=CO$_2$H, n=1)

(a) (3,5-Dibromo-4-(2-(4-iodo-benzoyl)-5-isopropyl-4-methoxy-phenoxy)-phenyl)-acetic acid methyl ester. This compound was prepared by the method described in example 1c from (3,5-dibromo-4-(5-isopropyl-4-methoxyphenoxy)-phenyl)-acetic acid methyl ester (50 mg, 0.11 mmol) and 4-iodobenzoyl chloride (141 mg, 0.53 mmol) to afford 60 mg (81%) (3,5-Dibromo-4-(2-(4-iodo-benzoyl)-5-isopropyl-4-methoxy-phenoxy)-phenyl)-acetic acid methyl ester as a white solid.

(b) (3,5-Dibromo-4-(2-(4-iodo-benzoyl)-5-isopropyl-4-methoxy-phenoxy)-phenyl)-acetic acid. This compound was prepared by the method described for example 12 from (3,5-dibromo-4-(2-(4-iodo-benzoyl)-5-isopropyl-4-methoxy-phenoxy)-phenyl)-acetic acid methyl ester (60 mg, 0.08 mmol) to afford 47 mg (81%) of the compound. $^1$H NMR (CD$_3$CN): d 7.90 (m, 2H), 7.56 (s, 2H), 7.52 (m, 2H), 7.06 (s, 1H), 6.29 (s, 1H), 3.81 (s, 3H), 3.57 (s, 2H), 3.23 (m, 1H), 1.03 (d, 6H).

EXAMPLE 30

(3,5-Dibromo-4-(2-(3-nitro-benzoyl)-5-isopropyl-4-methoxy-phenoxy)-phenyl)-acetic Acid (Structure 5 of Scheme 1, where R$_1$=R$_2$=Br, R$_3$=3-Nitrobenzoyl, R$_4$=Me, R$_5$=CO$_2$H, n=1)

(a) (3,5-Dibromo-4-(2-(3-nitro-benzoyl)-5-isopropyl-4-methoxy-phenoxy)-phenyl)-acetic acid methyl ester. This compound was prepared by the method described in example 1c from (3,5-Dibromo-4-(5-isopropyl-4-methoxy-phenoxy)-phenyl)-acetic acid methyl ester (100 mg, 0.21 mmol) and 3-nitrobenzoyl chloride (194 mg, 1.05 mmol) to afford 27 mg (21%) (3,5-Dibromo-4-(2-(3-nitro-benzoyl)-5-isopropyl-4-methoxy-phenoxy)-phenyl)-acetic acid methyl ester as a white solid.

(b) (3,5-Dibromo-4-(2-(3-nitro-benzoyl)-5-isopropyl-4-methoxy-phenoxy)-phenyl)-acetic acid. This compound was prepared by a similar method described for example 12 from (3,5-dibromo-4-(2-(3-nitro-benzoyl)-5-isopropyl-4-methoxy-phenoxy)-phenyl)-acetic acid methyl ester (27 mg, 0.043 mmol) to afford 19.7 mg (75%) of the compound. $^1$H NMR (CDCl$_3$): d 8.76 (m, 1H), 8.37 (m, 1H), 8.31 (m, 1H), 7.64 (m, 1H), 7.43 (s, 2H), 7.12 (s, 1H), 6.25 (s, 1H), 3.87 (s, 3H), 3.60 (s, 2H), 3.26 (m, 1H), 1.09 (d, 6H).

EXAMPLE 31

(3,5-Dibromo-4-(2-(3-trifluoromethyl-benzoyl)-5-isopropyl-4-methoxy-phenoxy)-phenyl)-acetic Acid (Structure 5 of Scheme 1, where R$_1$=R$_2$=Br, R$_3$=3-Trifluoromethyl-benzoyl, R$_4$=Me, R$_5$=CO$_2$H, n=1)

(a) (3,5-Dibromo-4-(2-(3-trifluoromethyl-benzoyl)-5-isopropyl-4-methoxy-phenoxy)-phenyl)-acetic acid methyl ester. This compound was prepared by the method described in example 1c from (3,5-dibromo-4-(5-isopropyl-4-methoxy-phenoxy)-phenyl)-acetic acid methyl ester (185 mg, 0.39 mmol) and 3-trifluoromethylbenzoyl chloride (404 mg, 1.94 mmol) to afford 218 mg (95%) (3,5-Dibromo-4-(2-(3-trifluoromethyl-benzoyl)-5-isopropyl-4-methoxy-phenoxy)-phenyl)-acetic acid methyl ester as a yellow solid.

(b) (3,5-Dibromo-4-(2-(3-trifluoromethyl-benzoyl)-5-isopropyl-4-methoxy-phenoxy)-phenyl)-acetic acid. This compound was prepared by a similar method described for example 12 from (3,5-dibromo-4-(2-(3-trifluoromethyl-benzoyl)-5-isopropyl-4-methoxy-phenoxy)-phenyl)-acetic acid methyl ester (205 mg, 0.35 mmol) to afford 135 mg (62%) of the compound. $^1$H NMR (CDCl$_3$): d 8.21 (m, 1H), 8.16 (m, 1H), 7.79 (m, 1H), 7.57 (m, 1H), 7.06 (s, 1H), 6.27 (s, 1H), 3.84 (s, 3H), 3.56 (s, 2H), 3.25 (m, 1H), 1.09 (d, 6H).

EXAMPLE 32

(3,5-Dibromo-4-(2-(3-hydroxy-benzoyl)-5-isopropyl-4-methoxy-phenoxy)-phenyl)-acetic Acid (Structure 5 of Scheme 1, where R$_1$=R$_2$=Br, R$_3$=3-Hydroxybenzoyl, R$_4$=Me, R$_5$=CO$_2$H, n=1)

(a) (4-(2-(3-Acetoxy-benzoyl)-5-isopropyl-4-methoxy-phenoxy)-3,5-dibromo-phenyl)-acetic acid methyl ester. This compound was prepared by the method described in example 1c from (3,5-dibromo-4-(5-isopropyl-4-methoxy-phenoxy)-phenyl)-acetic acid methyl ester (1.0 g, 2.1 mmol) and 3-acetoxy-benzoyl chloride (1.25 g, 6.3 mmol) to afford 50 mg (4%) (4-(2-(3-acetoxy-benzoyl)-5-isopropyl-4-methoxy-phenoxy)-3,5-dibromo-phenyl)-acetic acid methyl ester as a yellow solid.

(b) (3,5-Dibromo-4-(2-(3-hydroxy-benzoyl)-5-isopropyl-4-methoxy-phenoxy)-phenyl)-acetic acid. This compound was prepared by a similar method described for example 12 from (4-(2-(3-acetoxy-benzoyl)-5-isopropyl-4-methoxy-phenoxy)-3,5-dibromo-phenyl)-acetic acid methyl ester (50 mg, 0.079 mmol) to afford 22 mg (48%) of the compound. $^1$H NMR (CD$_3$SOCD$_3$): d 9.73 (s, 1H), 7.67 (s, 2H), 7.35 (m, 1H), 7.33 (s, 1H), 7.29 (m, 1H), 7.04 (m, 2H), 6.17 (s, 1H), 3.79 (s, 3H), 3.66 (s, 2H), 3.18 (m, 1H), 1.00 (d, 6H).

EXAMPLE 33

(3,5-Dibromo-4-(2-(3,3-dimethyl-butyryl)-5-isopropyl-4-methoxy-phenoxy)-phenyl)-acetic Acid (Structure 5 of Scheme 1, where $R_1=R_2=Br$, $R_3=3,3$-Dimethyl-butyryl, $R_4=Me$, $R_5=CO_2H$, n=1)

(a) (3,5-Dibromo-4-(2-(3,3-dimethyl-butyryl)-5-isopropyl-4-methoxy-phenoxy)-phenyl)-acetic acid methyl ester. This compound was prepared by the method described in example 1c from (3,5-dibromo-4-(5-isopropyl-4-methoxy-phenoxy)-phenyl)-acetic acid methyl ester (50 mg, 0.11 mmol) and 3,3-dimethyl-butyryl chloride (70 mg, 0.53 mmol) to afford 45 mg (74%) (3,5-dibromo-4-(2-(3,3-dimethyl-butyryl)-5-isopropyl-4-methoxy-phenoxy)-phenyl)-acetic acid methyl ester as a yellow solid.

(b) (3,5-Dibromo-4-(2-(3,3-dimethyl-butyryl)-5-isopropyl-4-methoxy-phenoxy)-phenyl)-acetic acid. This compound was prepared by the method described for example 12 from (3,5-dibromo-4-(2-(3,3-dimethyl-butyryl)-5-isopropyl-4-methoxy-phenoxy)-phenyl)-acetic acid methyl ester (25 mg, 0.04 mmol) to afford 20 mg (82%) of the compound. $^1$H NMR (CDCl$_3$): d 7.56 (s, 2H), 7.21 (s, 1H), 6.18 (s, 1H), 3.83 (s, 3H), 3.67 (s, 2H), 3.48 (m, 1H), 3.14 (s, 2H), 1.07 (s, 9H), 1.04 (d, 6H).

EXAMPLE 34

(3,5-Dibromo-4-(2-hexanoyl-5-isopropyl-4-methoxy-phenoxy)-phenyl)-acetic Acid (Structure 5 of Scheme 1, where $R_1=R_2=Br$, $R_3$=Hexanoyl, $R_4=Me$, $R_5=CO_2H$, n=1)

(a) (3,5-Dibromo-4-(2-hexanoyl-5-isopropyl-4-methoxy-phenoxy)-phenyl)-acetic acid methyl ester. This compound was prepared by the method described in example 1c from (3,5-dibromo-4-(5-isopropyl-4-methoxy-phenoxy)-phenyl)-acetic acid methyl ester (50 mg, 0.11 mmol) and hexanoyl chloride (71 mg, 0.53 mmol) to afford 28 mg (46%) (3,5-dibromo-4-(2-hexanoyl-5-isopropyl-4-methoxy-phenoxy)-phenyl)-acetic acid methyl ester as a yellow solid.

(b) (3,5-Dibromo-4-(2-hexanoyl-5-isopropyl-4-methoxy-phenoxy)-phenyl)-acetic acid. This compound was prepared by the method described for example 12 from (3,5-dibromo-4-(2-hexanoyl-5-isopropyl-4-methoxy-phenoxy)-phenyl)-acetic acid methyl ester (25 mg, 0.04 mmol) to afford 18 mg (74%) of the compound. $^1$H NMR (CDCl$_3$): d 7.57 (s, 2H), 7.37 (s, 1H), 6.19 (s, 1H), 3.84 (s, 3H), 3.68 (s, 2H), 3.17 (t, 2H), 1.74 (m, 2H), 1.34 (m, 4H), 1.01 (d, 6H), 0.87 (t, 3H).

EXAMPLE 35

(3,5-Dibromo-4-(2-(1-pyrrolidine-carbonyl)-5-isopropyl-4-methoxy-phenoxy)-phenyl)-acetic Acid (Structure 5 of Scheme 1, where $R_1=R_2=Br$, $R_3=1$-Pyrrolidinecarbonyl, $R_4=Me$, $R_5=CO_2H$, n=1)

(a) (3,5-Dibromo-4-(2-(1-pyrrolidine-carbonyl)-5-isopropyl-4-methoxy-phenoxy)-phenyl)-acetic acid methyl ester. This compound was prepared by the method described in example 1c from (3,5-dibromo-4-(5-isopropyl-4-methoxy-phenoxy)-phenyl)-acetic acid methyl ester (50 mg, 0.11 mmol) and 1-pyrrolidinecarbonyl chloride (71 mg, 0.53 mmol) to afford 21 mg (35%) (3,5-Dibromo-4-(2-(1-pyrrolidine-carbonyl)-5-isopropyl-4-methoxy-phenoxy)-phenyl)-acetic acid methyl ester as a yellow solid.

(b) (3,5-Dibromo-4-(2-(1-pyrrolidine-carbonyl)-5-isopropyl-4-methoxy-phenoxy)-phenyl)-acetic acid. This compound was prepared by a similar method described for example 12 from (3,5-dibromo-4-(2-(1-pyrrolidine-carbonyl)-5-isopropyl-4-methoxy-phenoxy)-phenyl)-acetic acid methyl ester (51 mg, 0.026 mmol) to afford 9 mg (61%) of the compound. $^1$H NMR (CDCl$_3$): d 7.38 (s, 2H), 6.90 (s, 1H), 6.24 (s, 1H), 3.81 (s, 3H), 3.68 (m, 4H), 3.55 (s, 2H), 3.16 (m, 2H), 1.91 (m, 4H), 1.01 (d, 6H).

EXAMPLE 36

(3,5-Dibromo-4-(2-(3,5-di-tert-butyl-benzoyl)-5-isopropyl-4-methoxy-phenoxy)-phenyl)-acetic Acid (Structure 5 of Scheme 1, where $R_1=R_2=Br$, $R_3=3,5$-di-tert-Butylbenzoyl, $R_4=Me$, $R_5=CO_2H$, n=1)

(a) (3,5-Dibromo-4-(2-(3,5-di-tert-butyl-benzoyl)-5-isopropyl-4-methoxy-phenoxy)-phenyl)-acetic acid methyl ester. This compound was prepared by the method described in example 1c from (3,5-dibromo-4-(5-isopropyl-4-methoxy-phenoxy)-phenyl)-acetic acid methyl ester (100 mg, 0.21 mmol) and 3,5-di-tert-butylbenzoyl chloride (185 mg, 0.73 mmol) to afford 111 mg (77%) (3,5-dibromo-4-(2-(3,5-di-tert-butyl-benzoyl)-5-isopropyl-4-methoxy-phenoxy)-phenyl)-acetic acid methyl ester as a white solid.

(b) (3,5-Dibromo-4-(2-(3,5-di-tert-butyl-benzoyl)-5-isopropyl-4-methoxy-phenoxy)-phenyl)-acetic acid. This compound was prepared by a similar method described for example 12 from (3,5-Dibromo-4-(2-(3,5-di-tert-butyl-benzoyl)-5-isopropyl-4-methoxy-phenoxy)-phenyl)-acetic acid methyl ester (55 mg, 0.80 mmol) to afford 49 mg (91%) of the compound. $^1$H NMR (CDCl$_3$): d 7.80 (m, 2H), 7.63 (m, 1H), 7.44 (s, 2H), 6.92 (s, 1H), 6.36 (s, 1H), 3.78 (s, 3H), 3.58 (s, 2H), 1.32(s, 18H), 1.09 (d, 6H).

EXAMPLE 37

(3,5-Dibromo-4-(2-(3,5-difluoro-benzoyl)-5-isopropyl-4-methoxy-phenoxy)-phenyl)-acetic Acid (Structure 5 of Scheme 1, where $R_1=R_2=Br$, $R_3=3,5$-Difluorobenzoyl, $R_4=Me$, $R_5=CO_2H$, n=1)

(a) (3,5-Dibromo-4-(2-(3,5-difluoro-benzoyl)-5-isopropyl-4-methoxy-phenoxy)-phenyl)-acetic acid methyl ester. This compound was prepared by the method described in example 1c from (3,5-dibromo-4-(5-isopropyl-4-methoxy-phenoxy)-phenyl)-acetic acid methyl ester (100 mg, 0.21 mmol) and 3,5-Difluorobenzoyl chloride (130 mg, 0.74 mmol) to afford 40 mg (31%) (3,5-Dibromo-4-(2-(3,5-difluoro-benzoyl)-5-isopropyl-4-methoxy-phenoxy)-phenyl)-acetic acid methyl ester as a white solid.

(b) (3,5-Dibromo-4-(2-(3,5-difluoro-benzoyl)-5-isopropyl-4-methoxy-phenoxy)-phenyl)-acetic acid. This compound was prepared by a similar method described for example 12 from (3,5-dibromo-4-(2-(3,5-difluoro-benzoyl)-5-isopropyl-4-methoxy-phenoxy)-phenyl)-acetic acid methyl ester (40 mg, 0.06 mmol) to afford 36 mg (92%) of the compound. $^1$H NMR (CDCl$_3$): d 7.50 (m, 3H), 7.46 (s, 2H), 7.03 (s, 1H), 6.97 (m, 1H), 6.25 (s, 1H), 3.84 (s, 3H), 3.60 (s, 2H), 3.24 (m, 1H), 1.06 (d, 6H).

EXAMPLE 38

(3,5-Dibromo-4-(5-isopropyl-4-methoxy-2-(3-methyl-benzyl)-phenoxy) phenyl)-acetic Acid (Structure 5 of Scheme 1, where $R_1=R_2=Br$, $R_3=3$-Methyl-benzyl, $R_4=Me$, $R_5=CO_2H$, n=1)

This compound was prepared by the method described in example 14a from (3,5-Dibromo-4-(5-isopropyl-4-methoxy-2-(3-methyl-benzoyl)-phenoxy) phenyl)-acetic acid (28 mg, 0.05 mmol) to afford 27 mg (99%) (3,5-Dibromo-4-(5-isopropyl-4-methoxy-2-(3-methyl-benzyl)-phenoxy) phenyl)-acetic acid as a yellow solid. $^1$H NMR (CDCl$_3$): d 7.54 (s, 2H), 7.19–7.14 (m, 3H), 6.99 (m, 1H), 6.63 (s, 1H), 6.13 (s, 1H), 4.12 (s, 2H), 3.70 (s, 3H), 3.65 (s, 2H), 3.14 (m, 1H), 2.31 (s, 3H), 1.02 (d, 6H).

EXAMPLE 39

(3,5-Dibromo-4-(2-(3-iodo-benzyl)-5-isopropyl-4-methoxy-phenoxy)-phenyl)-acetic Acid (Structure 5 of Scheme 1, where $R_1=R_2=Br$, $R_3$=3-Iodo-benzyl, $R_4$=Me, $R_5=CO_2H$, n=1)

(a) (3,5-Dibromo-4-(2-(3-iodo-benzyl)-5-isopropyl-4-methoxy-phenoxy)-phenyl)-acetic acid methyl ester. This compound was prepared by the method described in example 14a from (3,5-dibromo-4-(2-(3-iodo-benzyl)-5-isopropyl-4-methoxy-phenoxy)-phenyl)-acetic acid methyl ester (75 mg, 0.10 mmol) to afford 67 mg (91%) (3,5-Dibromo-4-(2-(3-iodo-benzyl)-5-isopropyl-4-methoxy-phenoxy)-phenyl)-acetic acid methyl ester as a yellow solid.

(b) (3,5-Dibromo-4-(2-(3-iodo-benzyl)-5-isopropyl-4-methoxy-phenoxy)-phenyl)-acetic acid. This compound was prepared by a similar method described for example 12 from (3,5-dibromo-4-(5-isopropyl-2-(3-iodo-benzyl)-4-methoxy-phenoxy) phenyl)-acetic acid methyl ester (67 mg, 0.10 mmol) to afford 62 mg (94%) of the compound. $^1$H NMR (CDCl$_3$): d 7.72 (m, 1H), 7.54 (s, 2H), 7.50, (m, 1H), 7.31 (m, 1H), 7.00 (m, 1H), 6.64 (s, 1H), 6.13 (s, 1H), 4.08 (s, 2H), 3.74 (s, 3H), 3.65 (s, 2H), 3.15 (m, 1H) , 1.02 (d, 6H).

EXAMPLE 40

(3,5-Dibromo-4-(5-isopropyl-4-methoxy-2-(3-methyl-benzoyl)-phenoxy)-phenyl)-propionic Acid (Structure 5 of Scheme 1, where $R_1=R_2=Br$, $R_3$=3-Methyl-benzoyl, $R_4$=Me, $R_5=CO_2H$, n=2)

(a) (3,5-Dibromo-4-(5-isopropyl-4-methoxy-phenoxy)-phenyl)-propionic acid methyl ester. This compound was prepared by the method described in example 1b from Bis(3-isopropyl-4-methoxyphenyl)iodonium tetrafluoroborate (600 mg, 1.2 mmol) and 3,5-dibromo-4-hydroxy-phenyl propionic acid methyl ester (264 mg, 0.8 mmol) to afford 301 mg (80%) of the compound (b) (3,5-Dibromo-4-(5-isopropyl-4-methoxy-2-(3-methyl-benzoyl)-phenoxy)-phenyl)-propionic acid methyl ester This compound was prepared by the method described in example 1c from (3,5-dibromo-4-(5-isopropyl-4-methoxy-phenoxy)-phenyl)-propionic acid methyl ester (100 mg, 0.21 mmol) and 3-methylbenzoyl chloride (112 mg, 0.72 mmol). 86 mg (69%) of the compound was obtained as a white solid.

(c) (3,5-Dibromo-4-(5-isopropyl-4-methoxy-2-(3-methyl-benzoyl)-phenoxy)-phenyl)-propionic acid. This compound was prepared by the method described for example 12 from (3,5-dibromo-4-(5-isopropyl-4-methoxy-2-(3-methyl-benzoyl)-phenoxy)-phenyl)-propionic acid methyl ester (82 mg, 0.14 mmol). 74 mg (92%) of the compound was obtained as a white solid. $^1$H NMR (CDCl$_3$): d 7.81 (m, 2H), 7.36 (s, 2H), 7.34–7.30 (m, 2H), 6.99 (s, 1H), 6.24 (s, 1H), 3.81 (s, 3H), 3.24 (m, 1H), 2.88 (m, 2H), 2.64 (m, 2H), 2.38 (s, 3H), 1.06 (d, 6H).

EXAMPLE 41

2-(3,5-Dibromo-4-(5-isopropyl-4-methoxy-2-(3-methyl-benzoyl)-phenoxy)-phenyl)-propionic Acid (Structure 5 of Scheme 1, where $R_1=R_2=Br$, $R_3$=3-Methyl-benzoyl, $R_4$=Me, $R_5=CO_2H$, n=2)

This compound was prepared by the method described for example 13 from 2-(3,5-dibromo-4-(5-isopropyl-4-methoxy-2-(3-methyl-benzoyl)-phenoxy)-phenyl)-propionic acid methyl ester (82 mg, 0.14 mmol). 74 mg (92%) of the compound was obtained as a white solid. $^1$H NMR (CDCl$_3$): d 7.80 (m, 2H), 7.47 (s, 2H), 7.29 (m, 2H), 7.00 (s, 1H), 6.25 (s, 1H), 3.82 (s, 3H), 3.65 (q, 1H), 3.24 (m, 1H), 2.38 (s, 3H), 1.47 (d, 3H), 1.06 (d, 6H).

EXAMPLE 42

(3,5-Dibromo-4-((5-isopropyl-4-methoxy-2-(3-(phenyl-ethynyl)-benzoyl)-phenoxy)-phenyl)-acetic Acid (Structure 5 of Scheme 1, where $R_1=R_2=Br$, $R_3$=3-(Phenyl-ethynyl)-benzoyl, $R_4$=Me, $R_5=CO_2H$, n=1)

(a) (3,5-Dibromo-4-((5-isopropyl-4-methoxy-2-(3-(phenyl-ethynyl)-benzoyl)-phenoxy)-phenyl)-acetic acid methyl ester. (3,5-Dibromo-4-(2-(3-iodo-benzoyl)-5-isopropyl-4-methoxy-phenoxy)-phenyl)-acetic acid methyl ester (75 mg, 0.10 mmol) and phenylacetylene (13 mg, 0.17 mmol) were dissolved in Et$_2$N (0.6 ml). PdCl$_2$(PPh$_3$)$_2$ (3.7 mg, 5 mol %) and CuI (2 mg, 10 mol %) were added subsequently. The reaction mixture was stirred at room temperature for 3h. The solvent was evaporated and the residue purified on silica gel (n-heptane/EtOAc 9:1) to afford 47 mg (65%) of the compound.

(b) (3,5-Dibromo-4-((5-isopropyl-4-methoxy-2-(3-(phenyl-ethynyl)-benzoyl)-phenoxy)-phenyl)-acetic acid. This compound was prepared by a similar method described for example 12 from (3,5-dibromo-4-((5-isopropyl-4-methoxy-2-(3-(phenyl-ethynyl)-benzoyl)-phenoxy)-phenyl)-acetic acid methyl ester (16 mg, 0.02 mmol) to afford 15 mg (96%) of the compound as a solid. $^1$H NMR (CDCl$_3$): d 8.16 (m, 1H), 7.98 (m, 1H), 7.68 (m, 1H), 7.51–7.25 (m, 8H), 7.05 (s, 1H), 6.25 (s, 1H), 3.84 (s, 3H), 3.59 (s, 2H), 3.25 (m, 1H), 1.07 (d, 6H).

EXAMPLE 43

(3,5-Dibromo-4-(2-(3-(3-hydroxy-phenyl-ethynyl)-benzoyl)-5-isopropyl-4-methoxy-phenoxy)-phenyl)-acetic Acid (Structure 5 of Scheme 1, where $R_1=R_2=Br$, $R_3$=3-(3-Hydroxy-phenyl-ethynyl)-benzoyl, $R_4$=Me, $R_5=CO_2H$, n=1)

(a) (3,5-Dibromo-4-(2-(3-(3-hydroxy-phenyl-ethynyl)-benzoyl)-5-isopropyl-4-methoxy-phenoxy) phenyl)-acetic acid methyl ester. This compound was prepared by the method described in example 42a from 3,5-dibromo-4-(2-(3-iodo-benzoyl)-5-isopropyl-4-methoxy-phenoxy)-phenyl)-acetic acid methyl ester (75 mg, 0.10 mmol) and 3-hydroxyphenylacetylene (51 mg, 0.13 mmol) to afford 60 mg (82%) of the compound.

(b) (3,5-Dibromo-4-(2-(3-(3-hydroxy-phenyl-ethynyl)-benzoyl)-5-isopropyl-4-methoxy-phenoxy)-phenyl)-acetic acid. This compound was prepared by a similar method described for example 12 from (3,5-dibromo-4-(2-(3-(3-hydroxy-phenyl-ethynyl)-benzoyl)-5-isopropyl-4-methoxy-phenoxy)-phenyl)-acetic acid methyl ester (30 mg, 0.04 mmol) to afford 22 mg (75%) of the compound as a solid. $^1$H NMR (CDCl$_3$): d 8.16 (m, 1H), 7.98 (m, 1H), 7.66 (m, 1H), 7.52–7.36 (m, 3H), 7.17 (m, 1H), 7.06 (m, 2H), 6.96 (m, 1H), 6.81 (m, 1H), 6.24 (s, 1H), 3.83 (s, 3H), 3.57 (s, 2H), 3.24 (m, 1H), 1.06 (d, 6H).

EXAMPLE 44

(3,5-Dibromo-4-(2-(3-ethynyl-benzoyl)-5-isopropyl-4-methoxy-phenoxy) phenyl)-acetic Acid (Structure 5 of Scheme 1, where $R_1=R_2=Br$, $R_3$=3-Ethynyl-benzoyl, $R_4$=Me, $R_5=CO_2H$, n=1)

(a) (3,5-Dibromo-4-(5-isopropyl-4-methoxy-2-(3-trimethylsilanylethynyl-benzoyl)-phenoxy) phenyl)-acetic acid. This compound was prepared by the method described in example 42a from (3,5-dibromo-4-(2-(3-iodo-benzoyl)-5-isopropyl-4-methoxy-phenoxy)-phenyl)-acetic acid methyl ester (75 mg, 0.10 mmol) and (trimethylsilyl) acetylene (17 mg, 0.17 mmol) to afford 15 mg (21%) of the compound.

(b) (3,5-Dibromo-4-(2-(3-ethynyl-benzoyl)-5-isopropyl-4-methoxy-phenoxy) phenyl)-acetic acid. This compound was prepared by a similar method described for example 12 from (3,5-dibromo-4-(5-isopropyl-4-methoxy-2-(3-trimethylsilanylethynyl-benzoyl)-phenoxy) phenyl)-acetic acid (11 mg, 0.016 mmol) to afford 9.4 mg (98%) of the compound as a white solid. $^1$H NMR (CDCl$_3$): d 8.10 (m, 1H), 8.0 (m, 1H), 7.64 (m, 1H), 7.44 (s, 2H), 7.39 (m, 1H), 7.03 (s, 1H), 6.24 (s, 1H), 4.08 (s, 2H), 3.83 (s, 3H), 3.58 (s, 2H), 3.24 (m, 1H), 3.07 (s, 1H), 1.06 (d, 6H).

EXAMPLE 45

(3,5-Dibromo-4-(2-(3-(3-hydroxy-prop-1-ynyl)-benzoyl)-5-isopropyl-4-methoxy-phenoxy)-phenyl)-acetic Acid (Structure 5 of Scheme 1, where $R_1$=$R_2$=Br, $R_3$=3-(3-Hydroxy-prop-1-ynyl)-benzoyl, $R_4$=Me, $R_5$=CO$_2$H, n=1)

(a) (3,5-Dibromo-4-(2-(3-(3-hydroxy-prop-1-ynyl)-benzoyl)-5-isopropyl-4-methoxy-phenoxy)-phenyl)-acetic acid methyl ester. This compound was prepared by the method described in example 42a from 3,5-dibromo-4-(2-(3-iodo-benzoyl)-5-isopropyl-4-methoxy-phenoxy)-phenyl)-acetic acid methyl ester (75 mg, 0.10 mmol) and propargyl alcohol (7.2 mg, 0.13 mmol) to afford 62 mg (92%) of the compound.

(b) (3,5-Dibromo-4-(2-(3-(3-hydroxy-prop-1-ynyl)-benzoyl)-5-isopropyl-4-methoxy-phenoxy)-phenyl)-acetic acid. This compound was prepared by a similar method described for example 12 from (3,5-dibromo-4-(2-(3-(3-hydroxy-prop-1-ynyl)-benzoyl)-5-isopropyl-4-methoxy-phenoxy)-phenyl)-acetic acid methyl ester (25 mg, 0.04 mmol) to afford 21 mg (86%) of the compound as a solid. $^1$H NMR (CDCl$_3$): d 8.05 (m, 1H), 7.97 (m, 1H), 7.43 (s, 2H), 7.39 (m, 1H), 7.02 (s, 1H), 6.25 (s, 1H), 4.46 (s, 2H), 3.83 (s, 3H), 3.58 (s, 2H), 3.24 (m, 1H), 1.07 (d, 6H).

EXAMPLE 46

(3,5-Dibromo-4-(5-isopropyl-4-methoxy-2-(3-(3-oxo-pent-1-enyl)-benzoyl)-phenoxy)-phenyl)-acetic Acid (Structure 5 of Scheme 1, where $R_1$=$R_2$=Br, $R_3$=3-(3-Oxo-pent-1-enyl)-benzoyl, $R_4$=Me, $R_5$=CO$_2$H, n=1)

(a) (3,5-Dibromo-4-(5-isopropyl-4-methoxy-2-(3-(3-oxo-pent-1-enyl)-benzoyl)-phenoxy)-phenyl)-acetic acid methyl ester. (3,5-dibromo-4-(2-(3-iodo-benzoyl)-5-isopropyl-4-methoxy-phenoxy)-phenyl)-acetic acid methyl ester (100 mg, 0.14 mmol), ethyl vinyl ketone (16 mg, 0.18 mmol), Pd(OAc)$_2$ (3.2 mg, 10 mol %) and PPh$_3$ (7.5 mg, 20 mol %) were dissolved in DMF (0.8 ml). Et$_3$N (72 mg, 0.71 mmol) was added and the reaction was stirred at 40° C. for 16h. The reaction was poured into water and the aqueous phase was extracted with EtOAc. Chromatography on silica gel (n-heptane/EtOAc, 8:2) gave 56 mg (60%) of the compound.

(b) (3,5-Dibromo-4-(5-isopropyl-4-methoxy-2-(3-(3-oxo-pent-1-enyl)-benzoyl)-phenoxy)-phenyl)-acetic acid. This compound was prepared by a similar method described for example 12 from (3,5-dibromo-4-(5-isopropyl-4-methoxy-2-(3-(3-oxo-pent-1-enyl)-benzoyl)-phenoxy)-phenyl)-acetic acid methyl ester (56 mg, 0.08 mmol) to afford 44 mg (80%) of the compound as a solid. $^1$H NMR (CDCl$_3$): d 8.14 (m, 1H), 8.00 (m, 1H), 7.70 (m, 1H), 7.58 (d, 1H), 7.47 (m, 1H), 7.43 (s, 2H), 7.05 (s, 1H) 6.78 (d, 1H) 6.27 (s, 1H) 3.84 (s, 3H), 3.57 (s, 2H), 3.25 (m, 1H), 2.66 (q, 2H), 1.12 (t, 3H), 1.07 (d, 6H).

EXAMPLE 47

2-(3,5-Dibromo-4-(5-isopropyl-4-methoxy-2-(3-methyl-benzoyl)-phenoxy) phenyl)-acetamide (Structure 5 of Scheme 1, where $R_1$=$R_2$=Br, $R_3$=3-Methyl-benzoyl, $R_4$=Me, $R_5$=CONH$_2$, n=1)

(3,5-Dibromo-4-(5-isopropyl-4-methoxy-2-(3-methyl-benzoyl)-phenoxy) phenyl)-acetic acid methyl ester (200 mg, 0.34 mmol) was treated with 25% NH$_4$OH in MeOH (10 ml) at 60° C. for 16h. The solvent was concentrated and the residue purified on silica gel to give 15 mg (7.7%) of the compound. $^1$H NMR (CDCl$_3$): d 7.80 (m, 2H), 7.44 (s, 2H), 7.32 (m, 2H), 6.98 (s, 1H), 6.27 (s, 1H), 5.63 (d, 2H), 3.81 (s, 3H), 3.47 (s, 2H), 3.24 (m, 1H), 2.38 (s, 3H) , 1.09 (d, 6H).

EXAMPLE 48

N-(4-(2-acetyl-4-hydroxy-5-isopropyl-phenoxy)-3,5-dibromo-phenyl)oxamic Acid (Structure 8 of Scheme 2 where $R_1$=NHCOCO$_2$H, $R_2$=CH$_3$CO)

(a) 2,6-dibromo-3'-isopropyl-4'-methoxy-4-nitrodiphenyl ether (Structure 7 of Scheme 2). The compound was prepared by the method described in example 1b from bis(3-isopropyl-4-methoxyphenyl)iodonium tetrafluoroborate (43.1 g, 84 mmol) and 2,6-dibromo-4-nitrophenol (16.7 g, 56.1) to give 23.0 g (97%) of 2,6-dibromo-3 -isopropyl-4'-methoxy-4-nitrodiphenyl ether as a yellow solid.

(b) 2'-Acetyl-2,6-dibromo-5'-isopropyl-4'-methoxy-4-nitrodiphenyl ether. This compound was prepared by the method described in example 1c from 2,6-dibromo-5'-isopropyl-4'-methoxy-4-nitrodiphenyl ether (3.6 g, 8.3 mmol) and acetyl chloride (1.6 g, 20.7 mmol) to give 1.19 g (29%) of 2'-acetyl-2,6-dibromo-5'-isopropyl-4'-methoxy-4-nitrodiphenyl ether as a white solid.

(c) 2'-Acetyl-4-amino-2,6-dibromo-5'-isopropyl-4'-methoxydiphenyl ether. 2'-Acetyl-2,6-dibromo-5'-isopropyl-4'-methoxy-4-nitrodiphenyl ether (283 mg, 0.58 mmol) was dissolved in 99.5% ethanol (5 ml) and tin(II) chloride dihydrate (655 mg, 2.9 mmol) was added. The solution was kept under N$_2$ and heated to 70° C. for 4 h. The reaction mixture was poured into ice water, made alkaline with 1M NaOH, extracted with EtOAc, washed with brine, dried over MgSO$_4$ and filtered. 252 mg (94%) 2'-acetyl-4-amino-2,6-dibromo-5'-isopropyl-4'-methoxydiphenyl ether was obtained as a white solid.

(d) N-(4-(2-acetyl-5-isopropyl-4-methoxyphenoxy)-3,5-dibromophenyl)-oxamic acid methyl ester. To 2'-acetyl-4-amino-2,6-dibromo-5'-isopropyl-4'-methoxydiphenyl ether (252 mg, 0.55 mmol) was added dimethyl oxalate (324 mg, 2.75 mmol) and the mixture was heated at reflux for 1 h. Excess of dimethyl oxalate was removed by evaporation and the crude product was purified on silica (80:20, petroleum ether/etyl acetate) to give 197 mg (66%) of N-(4-(2-acetyl-5-isopropyl-4-methoxyphenoxy)-3,5-dibromophenyl)-oxamic acid methyl ester.

(e) N-(4-(2-acetyl-4-hydroxy-5-isopropylphenoxy)-3,5-dibromophenyl)oxamic acid. The compound was prepared by the method described for example 5 from N-(4-(2-acetyl- 5-isopropyl-4-methoxyphenoxy)-3,5-dibromophenyl)-oxamic acid methyl ester) (100 mg, 0.18 mmol) to give 63 mg (66%) of N-(4-(2-acetyl-4-hydroxy-5-isopropylphenoxy)-3,5-dibromophenyl)oxamic acid as a white solid. $^1$H NMR (CD$_3$COCD$_3$): d 10.28 (s, 1H), 8.45 (s, 1H), 8.35 (s, 2 H), 7.35 (s, 1H), 6.31 (s, 1H), 3.22 (m, 1H), 1.05 (d, 6H).

EXAMPLE 49

N-(4-(2-ethyl-4-hydroxy-5-isopropyl-phenoxy)-3,5-dibromo-phenyl)oxamic Acid Methyl Ester
(Structure 8 of Scheme 2 where R$_1$=NHCOCO$_2$Me, R$_2$=CH$_3$CH$_2$)

(a) 4-amino-2,6-dibromo-2'-ethyl-5'-isopropyl-4'-methoxydiphenyl ether. To 2'-acetyl-4-amino-2,6-dibromo-5'-isopropyl-4'-methoxydiphenyl ether (0.500 g, 1.1 mmol), hydrazine hydrate (5.5 g, 110 mmol), potassium carbonate (5.5 g, 39.6 mmol) and diethylene glycol (10 ml) were added. The solution was heated at 150° C. for 16h and then to 200° C. for 4 hours. The reaction mixture was diluted with water, extracted with ethyl acetate, dried over magnesium sulphate, filtered and concentrated. The crude product was purified on a chromatotron (silica, 80:20, petroleum ether/ethyl acetate) producing 100 mg (0.22 mmol, 20%) of 4-amino-2,6-dibromo-2'-ethyl-5'-isopropyl-4'-methoxydiphenyl ether (b) 4-amino-2,6-dibromo-2'-ethyl-4'-hydroxy-5'-isopropyldiphenyl ether. The compound was prepared by the method described for example 5 from 4-Amino-2,6-dibromo-2'-ethyl-5'-isopropyl-4'-methoxydiphenyl ether (300 mg, 0.68 mmol) to afford 290 mg (100%) of 4-amino-2,6-dibromo-2'-ethyl-4'-hydroxy-5'-isopropyldiphenyl ether.

(c) N-(4-(2-ethyl-4-hydroxy-5-isopropyl-phenoxy)-3,5-dibromo-phenyl)oxamic acid methyl ester. 4-Amino-2,6-dibromo-2'-ethyl-4'-hydroxy-5'-isopropyldiphenyl ether (290 mg, 0.68 mmol) was allowed to react with dimethyl oxalate (400 mg, 3.40 mmol) according to the procedure in example 47d. The crude product was purified on a chromatotron (silica, 50:50, petroleum ether/ethyl acetate) giving 208 mg (0.41 mmol, 60%) N-(4-(2-ethyl-4-hydroxy-5-isopropylphenoxy)-3,5-dibromophenyl)oxamic acid methyl ester as a white solid. $^1$H NMR (CDCl$_3$): d 8.87 (s, 1H), 7.96 (s, 2H), 6.66 (s, 1H), 6.05 (s, 1H), 4.43 (s, 1H), 3.98 (s, 3H), 3.04 (m, 1H), 2.77 (q, 2H), 1.29 (t, 3H), 1.06 (d, 6H).

EXAMPLE 50

N-(4-(2-ethyl-4-hydroxy-5-isopropyl-phenoxy)-3,5-dibromo-phenyl)oxamic Acid (Structure 8 of
Scheme 2 where R$_1$=NHCOCO$_2$H, R$_2$=CH$_3$CH$_2$)

N-(4-(2-ethyl-4-hydroxy-5-isopropylphenoxy)-3,5-dibromophenyl)oxamic acid methyl ester (50 mg, 0.01 mmol), was dissolved in acetone (2 ml). 1M NaOH (1 ml) was added and the solution was stirred for 1 hour, cooled in an ice bath, acidified with 1M HCl, concentrated, extracted with ethyl acetate, dried over MgSO$_4$, filtered and evaporated to give 36 mg (74%) of N-(4-(2-ethyl-4-hydroxy-5-isopropylphenoxy)-3,5-dibromophenyl)oxamic acid. $^1$H NMR (CD$_3$COCD$_3$): d 10.24 (s, 1H), 8.33 (s, 2H), 6.77 (s, 1H), 6.12 (s, 1H), 3.16 (m, 1H), 2.74 (q, 2H), 1.27 (t, 3H), 1.04 (d, 6H).

EXAMPLE 51

N-(4-(2-Benzoyl-4-hydroxy-5-isopropyl-phenoxy)-3,5-dibromo-phenyl)oxamic Acid Methyl Ester
(Structure 8 of Scheme 2 where R$_1$=NHCOCO$_2$Me, R$_2$=Benzoyl)

(a) 2'-benzoyl-2,6-dibromo-5'-isopropyl-4'-methoxy-4-nitrodiphenyl ether. 2,6-Dibromo-3'-isopropyl-4'-methoxy-4-nitrodiphenyl ether (1,5 g, 3.45 mmol), was dissolved in dichloromethane (25 mL) then it was treated with benzoyl-chloride (1.3 g, 8.75 mmol) and titanium tetrachloride (3.3 g, 17.4 mmol) according to the procedure in example 1c. The crude product was purified on a chromatotron (silica, 97:3, petroleum ether/ethyl acetate) producing 600 mg (1.2 mmol, 35%) of 2'-benzoyl-2,6-dibromo-5'-isopropyl-4'-methoxy-4-nitrodiphenyl ether.

(b) 4-amino-2'-benzoyl-2,6-dibromo-5'-isopropyl-4'-methoxydiphenyl ether. 2'-Benzoyl-2,6-dibromo-5'-isopropyl-4'-methoxy-4-nitrodiphenyl ether (550 mg, 1.10 mmol) was dissolved in 99.5% ethanol (5 mL) and tin(II) chloride dihydrate (1000 mg, 4.4 mmol) was added. The reaction mixture was then treated according to the procedure in example 47c. The crude product was purified on a chromatotron (silica, 75:25, petroleum ether/ethyl acetate) producing 500 mg (1.06 mmol, 96%) of 4-amino-2'-benzoyl-2,6-dibromo-51-isopropyl-4'-methoxydiphenyl ether (c) 4-amino-2'-benzoyl-2,6-dibromo-4'-hydroxy-5'-isopropyldiphenyl ether. The compound was prepared by the method described for example 5 from 4-amino-2'-benzoyl-2,6-dibromo-5'-isopropyl-4'-methoxydiphenyl ether (200 mg 0.42 mmol) to give 137 mg (71%) of 4-amino-2'-benzoyl-2,6-dibromo-4'-hydroxy-5'-isopropyldiphenyl ether.

(d) N-(4-(2'-benzoyl-4'-hydroxy-5'-isopropyl-phenoxy)-3,5-dibromophenyl) oxamic acid methyl ester. 4-Amino-2'-benzoyl-2,6-dibromo-4'-hydroxy-5'-isopropyldiphenyl ether (750 mg, 1.49 mmol) was treated with dimethyl oxalate (526 mg, 4.45 mmol) according to the procedure in example 47d. The crude product was purified on a chromatotron (silica, 50:50, petroleum ether/ethyl acetate) producing 386 mg (0.65 mmol, 44%) of N-(4-(2'-benzoyl-4'-hydroxy-5'-isopropyl-phenoxy)-3,5-dibromophenyl)oxamic acid methyl ester as a white solid. $^1$H NMR (CDCl$_3$): d 8.89 (s, 1H), 7.96–8.02 (m, 2H), 7.88 (s, 2H), 7.39–7.54 (m, 3H), 7.02 (s, 1H), 6.23 (s, 1H), 5.74 (s, 1H), 3.98 (s, 3H), 3.18 (m, 1H), 1.06 (d, 6H).

EXAMPLE 52

N-(4-(2-benzoyl-4-hydroxy-5-isopropyl-phenoxy)-3,5-dibromo-phenyl)oxamic Acid (Structure 8 of
Scheme 2 where R$_1$=NHCOCO$_2$H, R$_2$=Benzoyl).

This compound was prepared by the method described for example 12 from N-(4-(2'-benzoyl-4'-hydroxy-5'-isopropyl-phenoxy)-3,5-dibromophenyl)oxamic acid methyl ester (10 mg, 0.017 mmol) to give 8 mg (84%) of N-(4-(2'-benzoyl-4'-hydroxy-5'-isopropyl-phenoxy)-3,5-dibromophenyl) oxamic acid as a white solid. $^1$H NMR (CD$_3$COCD$_3$): d 8.07 (s, 2H), 7.91–7.95 (m, 2H), 7.44–7.59 (m, 3H), 6.88 (s, 1H), 6.24 (s, 1H), 3.23 (m, 1H), 1.08 (d, 6H).

EXAMPLE 53

N-(4-(2-benzyl-4-hydroxy-5-isopropyl-phenoxy)-3,5-dibromo-phenyl)oxamic Acid Methyl Ester
(Structure 8 of Scheme 2 where R$_1$=NHCOCO$_2$Me, R$_2$=Benzyl)

(a) 4-amino-2'-benzyl-2,6-dibromo-5'-isopropyl-4'-methoxydiphenyl ether. 4-Amino-2'-benzoyl-2,6-dibromo-5'-isopropyl-4'-methoxydiphenyl ether (280 mg, 0.59 mmol) was dissolved in diethylene glycol (30 mL). To the solution was added hydrazine hydrate (3 mL, 59 mmol) and potassium carbonate (3 g). The reaction mixture was treated according to the procedure in example 48a. The crude product was purified on a chromatotron (silica, 60:40, petroleum ether/ethyl acetate) producing 189 mg (0.41 mmol, 70%) of 4-amino-2'-benzyl-2,6-dibromo-5'-isopropyl-4'-methoxydiphenyl ether as a white solid.

(b) 4-amino-2'-benzyl-2,6-dibromo-4'-hydroxy-5'-isopropyldiphenyl ether. The compound was prepared by the method described for example 5 from 4-Amino-2'-benzyl-2,6-dibromo-5'-isopropyl-4'-methoxydiphenyl ether (189 mg, 0.41 mmol) to give 150 mg (82%) of crude 4-amino-2'-benzyl-2,6-dibromo-4'-hydroxy-5'-isopropyldiphenyl ether as a white solid.

(c) N-(4-(2'-benzyl-4'-hydroxy-5'-isopropylphenoxy)-3,5-dibromo phenyl)oxamic acid methyl ester. 4-Amino-2'-benzyl-2,6-dibromo-4'-hydroxy-5'-isopropyldiphenyl ether (150 mg, 0.33 mmol), obtained in example 52b, was treated with dimethyl oxalate (800 mg, 6.8 mmol) according to the procedure in example 47d. The crude product was purified on a chromatotron (silica, 75:25, petroleum ether/ethyl acetate) to give 50 mg (27%) of N-(4-(2'-benzyl-4'-hydroxy-5'-isopropylphenoxy)-3,5-dibromophenyl)oxamic acid methyl ester $^1$H NMR (CD$_3$COCD$_3$): d 8.29 (s, 2H), 7.85–7.88 (m, 2H), 7.28–7.37 (m, 3H), 6.61 (s, 1H), 6.18 (s, 1H), 4.10 (s, 2H), 3.90 (s, 3H), 3.16 (m, 1H), 1.04 (d, 6H).

EXAMPLE 54

N-(4-(2-benzyl-4-hydroxy-5-isopropyl-phenoxy)-3,5-dibromo-phenyl)oxamic Acid (Structure 8 of Scheme 2 where R$_1$=NHCOCO$_2$H, R$_2$=Benzyl)

Methyl-N-(3,5-dibromo-4-(2'-benzyl-4'-hydroxy-5'-isopropylphenoxy)-phenyl)-oxamate (25 mg, 0.043 mmol) was dissolved in acetone (2 ml) and 1M sodium hydroxide (1 ml) was added dropwise. The reaction mixture was treated according to the procedure in example 7. This produced 15 mg (62%) of N-(4-(2'-benzyl-4'-hydroxy-5'-isopropylphenoxy)-3,5-dibromophenyl)oxamic acid as a white solid. $^1$H NMR (CD$_3$COCD$_3$): d 8.32 (s, 2H), 7.85–7.86 (m, 2H), 7.27–7.34 (m, 3H), 6.61 (s, 1H), 6.19 (s, 1H), 4.10 (s, 2H), 3.19 (m, 1H), 1.04 (d, 6H).

What is claimed is:

1. A compound having the formula:

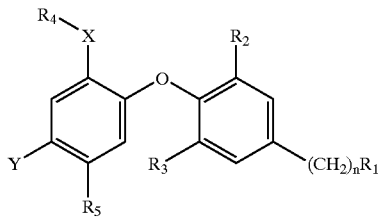

wherein
R$_1$ is an aliphatic hyrdocarbon, an aromatic hyrdocarbon, carboxylic acid or ester thereof, alkenyl carboxylic acid or ester thereof, oxamic acid or ester thereof, hydroxy, halogen, acetamido, or cyano, and all stereoisomers thereof;
R$_2$ and R$_3$ are the same or different and are hydrogen, halogen, alkyl of 1 to 4 carbons or cycloalkyl of 3 to 5 carbons, at least one of R$_2$ and R$_3$ being other than hydrogen;
X is carbonyl or methylene;
R$_4$ is an aliphatic, aromatic, or heteroaromatic;
R$_5$ is halogen, alkyl of 1 to 4 carbons or cycloalkyl of 3 to carbons;

Y is hydroxyl, methoxy, amino, or alkyl amino; and
n is an integer from 0 to 4.

2. The compound as defined in claim 1, wherein n is 0–2.
3. The compound as defined in claim 1 wherein R$_2$ and R$_3$ are each independently halogen.
4. The compound as defined in claim 1 wherein R$_2$ and R$_3$ are each independently an alkyl group.
5. The compound as defined in claim 1 wherein one of R$_2$ and R$_3$ is an alkyl group and the other is a halogen.
6. The compound as defined in claim 1 wherein one of R$_2$ and R$_3$ is an alkyl group and the other is a hydrogen.
7. The compound as defined in claim 1 wherein one of R$_2$ and R$_3$ is a halogen and the other is a hydrogen.
8. The compound as defined in claim 1 wherein R$_2$ and R$_3$ are independently chlorine, bromine, ethyl, isopropyl, or t-butyl.
9. The compound as defined in claim 1 wherein R$_5$ is isopropyl.
10. The compound as defined in claim 1 wherein R$_1$ is carboxyl, halogen, hydroxy, cyano, or an alkenoic acid residue.
11. The compound as defined in claim 1 which is
4-(2-benzoyl-4-hydroxy-5-isopropyl-phenoxy)-3,5-dibromo-benzoic acid methyl ester,
(4-(2-benzoyl-5-isopropyl-4-methoxy-phenoxy)-3,5-dibromo-phenyl)-acetic acid methyl ester,
4-(2-benzoyl-5-isopropyl-4-methoxy-phenoxy)-3,5-dimethyl-benzoic acid methyl ester,
(4-(2-(4-chlorophenylacetoyl)-5-isopropyl-4-methoxy-phenoxy)-3,5-dibromo-phenyl)-acetic acid methyl ester,
(4-(2-benzoyl-4-hydroxy-5-isopropyl-phenoxy)-3,5-dibromo-phenyl)-acetic acid methyl ester,
4-(2-benzoyl-4-hydroxy-5-isopropyl-phenoxy)-3,5-dibromo-benzoic acid, n=0,
(4-(2-benzoyl-4-hydroxy-5-isopropyl-phenoxy)-3,5-dibromo-phenyl)-acetic acid,
(4-(3-benzyl-4-hydroxy-5-isopropyl-phenoxy)-3,5-dibromo-phenyl)-acetic acid,
4-(4-hydroxy-5-isopropyl-2-(2-naphthoyl)phenoxy)-3,5-dibromo-phenyl-acetic acid,
4-(2-(4-tertiarybutylbenzoyl)-4-hydroxy-5-isopropyl-phenoxy)-3,5-dibromo-phenyl-acetic acid,
(4-(2-benzoyl-5-isopropyl-4-methoxy-phenoxy)-3,5-dibromo-phenyl)-acetic acid,
2-(3,5-dibromo-4-(2-(hydroxy-phenyl-methyl)-5-isopropyl-4-methoxy-phenoxy)-phenyl)-ethanol,
2-(4-(2-benzyl-5-isopropyl-4-methoxy-phenoxy)-3,5-dibromo-phenyl)-ethanol,
(4-(2-benzyl-5-isopropyl-4-methoxy-phenoxy)-phenyl)-acetic acid,
4-(2-benzoyl-5-isopropyl-4-methoxy-phenoxy)-3,5-dimethyl-benzoic acid,
4-(2-benzoyl-5-isopropyl-4-methoxy-phenoxy)-3,5-diisopropyl-benzoic acid,
(3,5-dibromo-4-(2-(2-fluoro-benzoyl)-5-isopropyl-4-methoxy-phenoxy)-phenyl)-acetic acid,
(3,5-dibromo-4-(2-(3-fluoro-benzoyl)-5-isopropyl-4-methoxy-phenoxy)-phenyl)-acetic acid,
(3,5-dibromo-4-(2-(4-fluoro-benzoyl)-5-isopropyl-4-methoxy-phenoxy)-phenyl)-acetic acid,
(3,5-dibromo-4-(5-isopropyl-4-methoxy-2-(2-methyl-benzoyl)-phenoxy)-phenyl)-acetic acid, (3,5-dibromo-4-(5 -isopropyl-4-methoxy-phenoxy-2-(3-methyl-benzoyl)-phenoxy)-phenyl)-acetic acid,
(3,5-dibromo-4-(5-isopropyl-4-methoxy-2-(4-methyl-benzoyl)-phenoxy)-phenyl)-acetic acid,
(3,5-dibromo-4-(2-(4-diphenylacetoyl)-5-isopropyl-4-methoxy-phenoxy)-phenyl)-acetic acid,
(4-(2-(3-chloro-benzoyl)-5-isopropyl-4-methoxy-phenoxy)-3,5 dibromo-phenyl)-acetic acid,
(4-(2-(4-chloro-benzoyl)-5-isopropyl-4-methoxy-phenoxy)-3,5 dibromo-phenyl)-acetic acid,
(4-(2-(3-bromo-benzoyl)-5-isopropyl-4-methoxy-phenoxy)-3,5 dibromo-phenyl)-acetic acid,
3,5-dibromo-4-(2-(3-iodo-benzoyl)-5-isopropyl-4-methoxy-phenoxy)-phenyl)-acetic acid,
3,5-dibromo-4-(2-(4-iodo-benzoyl)-5-isopropyl-4-methoxy-phenoxy)-phenyl)-acetic acid,
3,5-dibromo-4-(2-(3-nitro-benzoyl)-5-isopropyl-4-methoxy-phenoxy)-phenyl)-acetic acid,
3,5-dibromo-4-(2-(3-trifluoromethyl-benzoyl)-5-isopropyl-4-methoxy-phenoxy)-phenyl)-acetic acid,
3,5-dibromo-4-(2-(3-hydroxy-benzoyl)-5-isopropyl-4-methoxy-phenoxy)-phenyl)-acetic acid,
3,5-dibromo-4-(2-(3,3-dimethyl-butyryl)-5-isopropyl-4-methoxy-phenoxy)-phenyl)-acetic acid,
(3,5-dibromo-4-(2-hexanoyl-5-isopropyl-4-methoxy-phenoxy)-phenyl)-acetic acid,
(3,5-dibromo-4-(2-( 1-pyrrolidine-carbonyl)-5-isopropyl-4-methoxy-phenoxy)-phenyl)-acetic acid,
(3,5-dibromo-4-(2-(3,5-di-tert-butyl-benzoyl)-5-isopropyl-4-methoxy-phenoxy)-phenyl)-acetic acid,
(3,5-dibromo-4-(2-(3,5-difluoro-benzoyl)-5-isopropyl-4-methoxy-phenoxy)-phenyl)-acetic acid,
(3,5-dibromo-4-(5-isopropyl-4-methoxy-2-(3-methyl-benzyl)-phenoxy)-phenyl)-acetic acid,
(3,5-dibromo-4-(2-(3-iodo-benzyl)-5-isopropyl-4-methoxy-phenoxy)-phenyl)-acetic acid,
(3,5-dibromo-4-(5-isopropyl-4-methoxy-2-(3-methyl-benzoyl)-phenoxy)-phenyl)-propionic acid,
2-(3,5-dibromo-4-(5-isopropyl-4-methoxy-2-(3-methyl-benzoyl)-phenoxy)-phenyl)-propionic acid,
(3,5-dibromo-4-(5-isopropyl-4-methoxy-2-(3(phenyl-ethynyl)-benzoyl)-phenoxy)-phenyl)-acetic acid,
(3,5-dibromo-4-(2-(3-(3-hydroxy-phenyl-ethynyl)-benzoyl)-5-isopropyl-4-methoxy-phenoxy)-phenyl)-acetic acid,
(3,5-dibromo-4-(2-(3-ethynyl-benzoyl)-5-isopropyl-4-methoxy-phenoxy)-phenyl)-acetic acid,
(3,5-dibromo-4-(2-(3-(3-hydroxy-prop-1-ynyl)-benzoyl)-5-isopropyl-4-methoxy-phenoxy)-phenyl)-acetic acid,
(3,5-dibromo-4-(5-isopropyl-4-methoxy-2-(3-(3-oxo-pent-1-enyl)-benzoyl)-phenoxy)-phenyl)-acetic acid,
2-(3,5-dibromo-4-(5-isopropyl-4-methoxy-2-(3-methyl-benzoyl)-phenoxy)-phenyl)-acetamide,
n-(4-(2-acetyl-4-hydroxy-5-isopropyl-phenoxy)-3,5-dibromo-phenyl)oxamic acid,
n-(4-(2-ethyl-4-hydroxy-5-isopropyl-phenoxy)-3,5-dibromo-phenyl)oxamic acid methyl ester,
n-(4-(2-ethyl-4-hydroxy-5-isopropyl-phenoxy)-3,5-dibromo-phenyl)oxamic acid,
n-(4-(2-benzoyl-4-hydroxy-5-isopropyl-phenoxy)-3,5-dibromo-phenyl)oxamic acid methyl ester,
n-(4-(2-benzoyl-4-hydroxy-5-isopropyl-phenoxy)-3,5-dibromo-phenyl)oxamic acid,
n-(4-(2-benzyl-4-hydroxy-5-isopropyl-phenoxy)-3,5-dibromo-phenyl)oxamic acid methyl ester,
n-(4-(2-benzyl-4-hydroxy-5-isopropyl-phenoxy)-3,5-dibromo-phenyl)oxamic acid, or a pharmaceutically acceptable salt thereof.

12. A compound as defined in claim 1 having the structure

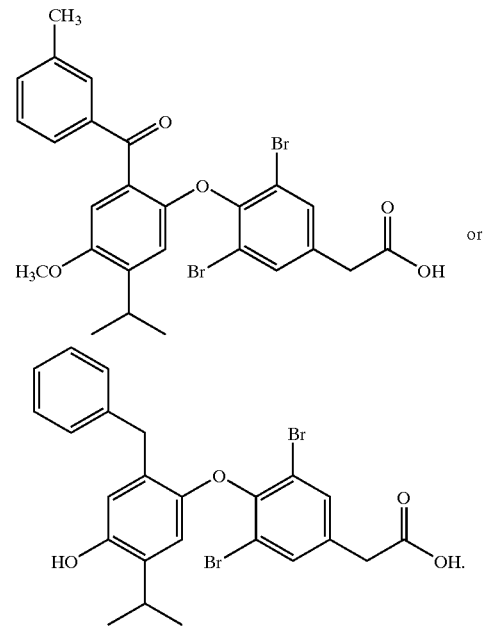

13. A method for inhibiting or treating diseases associated with a metabolism dysfunction which is dependent on the expression of a glucocorticoid receptor regulated gene which comprises administering to a patient in need of treatment a therapeutically effective amount of a compound as defined in claim 1.

14. The method as defined in claim 13 wherein the disease is associated with a metabolism dysfunction or which is dependent on the expression of a glucocorticoid receptor regulated gene is diabetes, Cushing's syndrome, or inflammation.

15. The method according to claim 14, in which the disease or disorder is selected from Type 1 insulin dependent diabetes, Type 2 non-insulin dependent diabetes, Cushing's syndrome, inflammation, or other endocrine disorders related to glucocorticoid hormones.

16. A method for inhibiting or treating a disease associated with a metabolism dysfunction which is dependent on the expression of a thyroid receptor regulated gene which comprises administering to a patient in need of treatment a therapeutically effective amount of a compound as defined in claim 1.

17. The method as defined in claim 16 wherein the disease is associated with a metabolism dysfunction or which is dependent on the expression of a thyroid receptor regulated gene is diabetes or inflammation.

18. The method according to claim 16, in which the disease or disorder is selected from hypercholesterolemia, obesity, skin disorders, glaucoma, or other endocrine disorders related to thyroid hormone.

* * * * *